(12) United States Patent
Mollerup et al.

(10) Patent No.: US 9,447,163 B2
(45) Date of Patent: Sep. 20, 2016

(54) PURIFICATION OF INSULIN

(75) Inventors: Joergen M. Mollerup, Bagsvaerd (DK); Soeren Soendergaarad Frederiksen, Copenhagen (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 13/980,969

(22) PCT Filed: Feb. 1, 2012

(86) PCT No.: PCT/EP2012/051662
§ 371 (c)(1),
(2), (4) Date: Nov. 20, 2013

(87) PCT Pub. No.: WO2012/104339
PCT Pub. Date: Aug. 9, 2012

(65) Prior Publication Data
US 2014/0073759 A1 Mar. 13, 2014

Related U.S. Application Data

(60) Provisional application No. 61/439,544, filed on Feb. 4, 2011.

(30) Foreign Application Priority Data

Feb. 1, 2011 (EP) .................................. 11152910

(51) Int. Cl.
C07K 14/62 (2006.01)
C07K 14/625 (2006.01)

(52) U.S. Cl.
CPC ............. *C07K 14/62* (2013.01); *C07K 14/625* (2013.01)

(58) Field of Classification Search
None
See application file for complete search history.

(56) References Cited

U.S. PATENT DOCUMENTS

| | | | |
|---|---|---|---|
| 3,649,456 A | 3/1972 | de Benneville | |
| 3,907,676 A | 9/1975 | Jorgensen | |
| 4,129,560 A | 12/1978 | Zoltobrocki | |
| 5,122,603 A | 6/1992 | Larner et al. | |
| 5,278,284 A | 1/1994 | Lusk et al. | |
| 5,504,188 A | 4/1996 | Baker et al. | |
| 5,633,350 A | 5/1997 | Fischer et al. | |
| 6,117,983 A | 9/2000 | Cowgill et al. | |
| 6,451,987 B1 | 9/2002 | Staby | |
| 2003/0216543 A1 | 11/2003 | Wang et al. | |
| 2005/0080000 A1 | 4/2005 | Thurow et al. | |
| 2006/0167221 A1 | 7/2006 | Sahib et al. | |

FOREIGN PATENT DOCUMENTS

| | | |
|---|---|---|
| CN | 101173006 A | 5/2008 |
| EP | 1071703 A1 | 1/2001 |
| EP | 1666048 A2 | 6/2006 |
| ES | 455065 A1 | 5/1978 |
| FR | 2375193 A1 | 7/1978 |
| GB | 694530 A | 7/1953 |
| GB | 729670 A | 5/1955 |
| GB | 2173503 A | 10/1986 |
| JP | S63-280100 A | 11/1988 |
| JP | 2008/520628 A | 6/2008 |
| JP | 2009/522231 A | 6/2009 |
| JP | 2009/536179 A | 10/2009 |
| RU | 2122549 C1 | 11/1998 |
| RU | 2322504 C1 | 4/2008 |
| WO | 98/34953 A1 | 8/1998 |
| WO | 2008/127305 A2 | 10/2008 |
| WO | 2008/152106 A1 | 12/2008 |
| WO | WO 2008152106 A1 * | 12/2008 |
| WO | WO 2009060071 A1 * | 5/2009 |

OTHER PUBLICATIONS

TSK-GEL SEC Column product information, "Get the most from Size Exclusion Chromatography," Brochure B04L01B, published by Tosoh Bioscience, pp. 1-16 Accessed Jan. 9, 2015 at URL: wolfson.huji.ac.il/purification/PDF/Gel_Filtration/TOSOH_GelFiltrationIII.pdf.*

Biological Buffers, Applichem, pp. 1-20 (2008) accessed at URL applichem.com/fileadmin/Broschueren/BioBuffer.pdf on Jan. 9, 2015.*

Tantipolphan R et al., Journal of Pharmaceutical and Biomedical Analysis, "Elution Behavior of Insulin on High-Performance Size Exclusion Chromatography at Neutral PH", 2010, vol. 52, No. 2, pp. 195-202.

Brange, -, "Galenics of Insulin", 1987.

Georges Guiochon, Journal of Chromatography A, "The Limits of the Separation Power of Unidimensional Column Liquid Chromatography", 2006, vol. 1126, pp. 6-49.

Helmerhorst E et al., Archives of Biochemistry and Biophysics, "The Self-Association of Insulin: Determinations Based on a Differential Gel Adsorption Procedure", 1986, vol. 245, No. 1, pp. 238-247.

Jørgen M. Mollerup, Chemical Engineering and Technology, "A Review of the Thermodynamics of Protein Association to Ligands, Protein Adsorption, and Adsorption Isotherms", 2008, vol. 31, No. 6, pp. 864-874.

(Continued)

*Primary Examiner* — Julie Ha
*Assistant Examiner* — Kristina M Hellman
(74) *Attorney, Agent, or Firm* — Rosemarie R. Wilk-Orescan

(57) ABSTRACT

The present application discloses a chromatographic process for separating protein components of a protein-containing solution, the solution comprising an insulin peptide and one or more di- or polyvalent metal ions, the insulin peptide being capable of self-association and/or structural change in the presence of di- or polyvalent metal ions, the process comprising the steps of: a) applying the protein-containing solution to a column of a chromatographic solid phase material, wherein the loading of the insulin peptide is at least 6.0 g per liter of column volume ($g/L_{CV}$); and b) eluting the insulin peptide from the solid phase material using an eluent having a pH of at the most 8.5; and collecting a pool of the insulin peptide corresponding to at least 75% by weight of the insulin peptide applied to the column in step (a).

11 Claims, 4 Drawing Sheets

(56) References Cited

OTHER PUBLICATIONS

Mollerup, J.M. et al., Journal of Liquid Chromatography and Related Technologies, "Use of Quality by the Design for the Modelling of Chromatographic Separations", 2009, vol. 32, pp. 1577-1597.

Søren Hvidt, Biophysical Chemistry, "Insulin Association in Neutral Solutions Studied by Light Scattering", 1991, vol. 39, No. 2, pp. 205-213.

* cited by examiner

Figure 1. Insulin peak profile at pH 6.4 giving a fronting peak in the presence of Zn2+ in the mobile phase, i.e. the protein-containing solution. The experiments at pH 6.4 were repeated at a high load, 12 g/L (dashed & full line) and at a low load, 8 g/L (dash dot & dash dot dot). The loads are proportional to the areas below the curves.
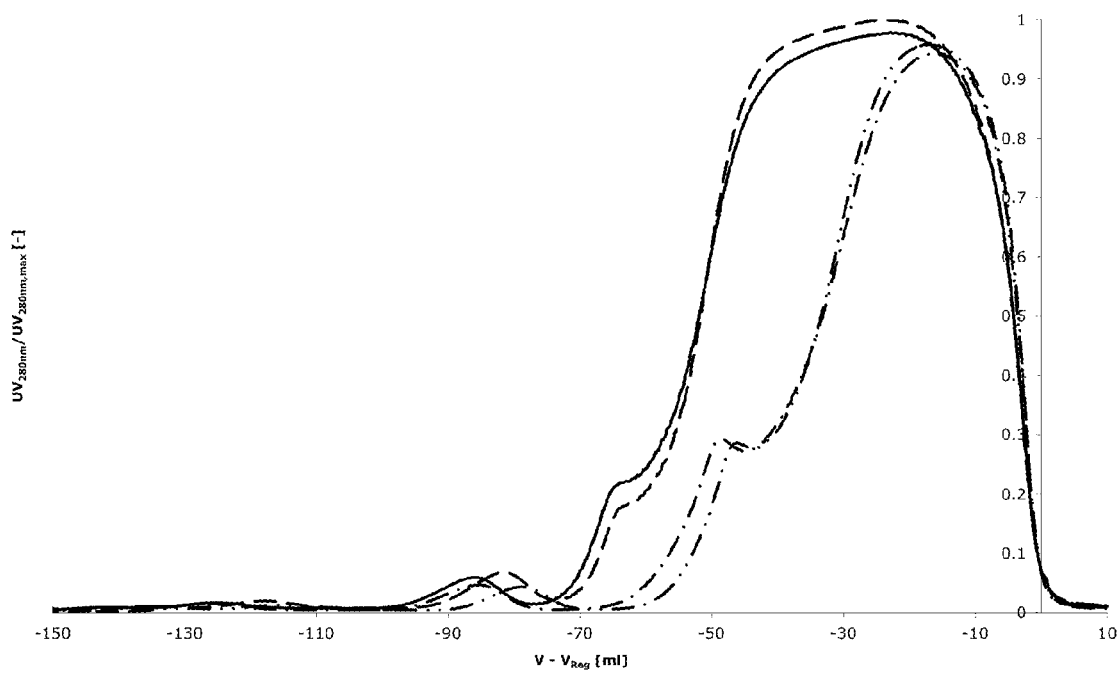

Figure 2. Insulin peak profile at pH 6.8 giving a tailing peak in the presence of Zn2+ in the mobile phase, i.e. the protein-containing solution. The experiments at pH 6.8 were repeated three times at a medium load, 10 g/L (dashed, full, and dash dot lines). The loads are proportional to the area below the curves.
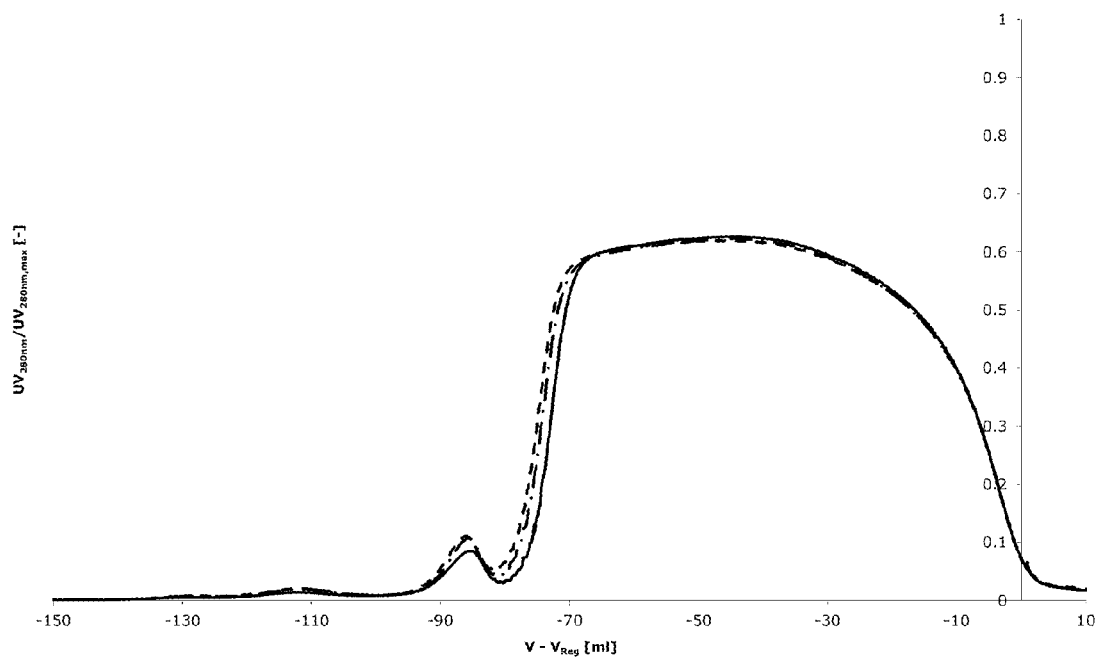

Figure 3. Insulin peak profile at pH 7.2 giving a tailing peak in the presence of Zn2+ in the mobile phase, i.e. the protein-containing solution. The experiments at pH 7.2 were repeated at a high load, 12 g/L (dashed & full line) and at a low load, 8 g/L (dash dot & dash dot dot). The loads are proportional to the areas below the curves.
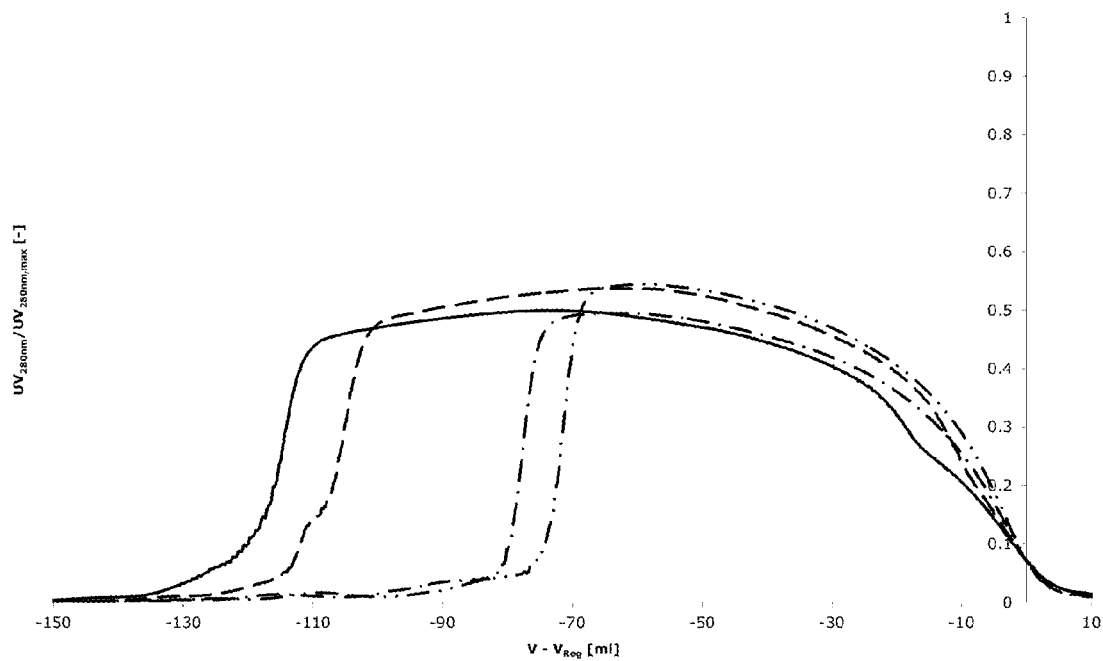

Figure 4. Chromatogram of experiment with Zn- balance. X-axis is the fraction number as given in the table in example 2 and Y-axis is the normalized UV-absorbance (as in figure 2). The chromatogram corresponds to the chromatograms of the experiments in figure 2.
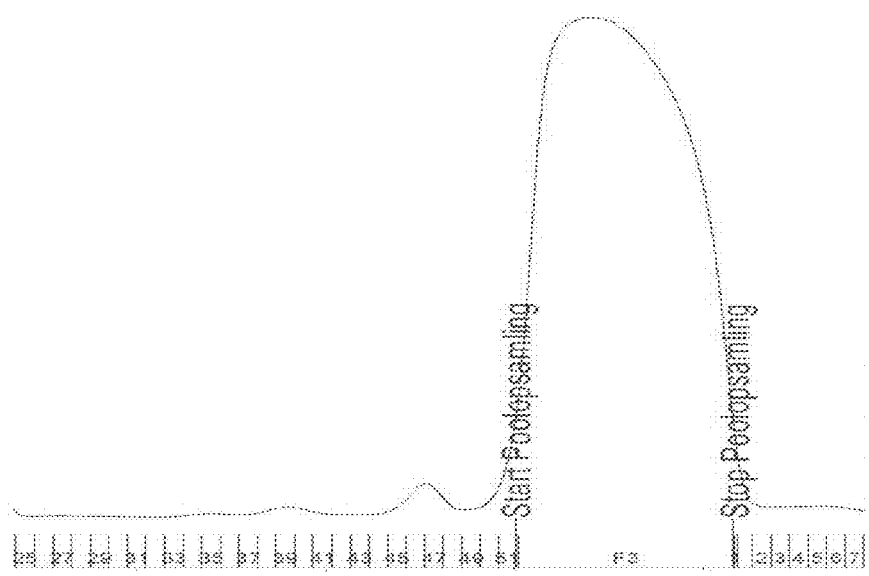

PURIFICATION OF INSULIN

CROSS-REFERENCE TO RELATED APPLICATIONS

This application is a 35 U.S.C. §371 National Stage application of International Application PCT/EP2012/051662 (WO 2012/104339 A1), filed Feb. 1, 2012, which claimed priority of European Patent Application 11152910.3, filed Feb. 1, 2011; this application claims priority under 35 U.S.C. §119 of U.S. Provisional Application 61/439,544; filed Feb. 4, 2011.

FIELD OF THE INVENTION

The present invention relates to chromatographic process for separating protein components of a protein-containing solution, in particular for isolating an insulin peptide in view of related impurities.

BACKGROUND OF THE INVENTION

Purification of recombinant proteins and peptides for pharmaceutical use are mainly performed using liquid chromatographic methods. Chromatographic methods are characterised by their stationary phase attributes, e.g. reversed phase chromatography for hydrophobic chromatographic resins, however, a number of parameters affect separation such as the mobile phase composition. Ion-exchange chromatography (IEC) is characterised by a charged surface of the stationary phase and the use of buffer, salt and control of pH for the mobile phase composition. IEC has proven very efficient in separation of both related and unrelated impurities, however, some impurities may still be very difficult to remove, e.g. if the same charge of target polypeptide and impurity is present.

GB 694530 and GB 729670 describe the crystallisation of insulin in the presence of quinoline or acridine-like substances and of phenolic nature, respectively, also in the presence of zinc.

U.S. Pat. No. 5,504,188 describes the preparation of insulin analogue crystals (LysPro) at pH 5.5-6.5 in the presence of (among others) zinc ions.

WO 98/34953 describes the crystallisation of a protein with lysine side-chain carrying a lipophilic substituent (insulin detemir) in a solution containing zinc ions, crystallisation being accomplished by adjusting solution pH from acidic to pH 7-10.

U.S. Pat. No. 3,907,676 discloses a process of reducing the antigenicity of insulin recovered from pancreas glands of domestic mammals, particularly pork and bovine pancreas glands, and containing antigenic insulin-like substances with a molecular weight about 6,000 together with some antigenic proteins of pancreatic origin with a molecular weight above 6,000. The reduction in antigenicity is obtained by subjecting the insulin to column chromatography on an anion exchanger which is preferably strongly basic while using a water-containing monohydric aliphatic alcohol as eluent, and collecting the eluate fractions containing insulin free or essentially free of the impurities referred to.

EP 1 071 703 disclose that addition of calcium ions to the mobile phase have shown to provide an improved selectivity between glycosylated and non-glycosylated species (specifically for insulin) compared to conventional RPC methods (employing monovalent ions).

U.S. Pat. No. 3,649,456 basically describes the buffer exchange of a polypeptide on a RPC-like stationary phase from an aqueous solution to organic solvent containing solution in the presence of various salts including calcium chloride.

U.S. Pat. No. 5,633,350 describes the separation of K-vitamin dependent proteins from non-K-vitamin dependent proteins in the presence of calcium ions on ion-exchange resins.

GB 2173503A describes a process for the purification of insulin using a weakly acid cation exchanger preferably with a hydrophobic matrix is provided. Fractionation of the insulin is obtained by step-wise or continuous alteration of the concentration of the solvent in the acid pH range.

U.S. Pat. No. 4,129,560 describes a process for the purification of high molecular weight peptides, which have a tendency to associate, by ion exchanger chromatography in aqueous buffered solvents on acid or basic ion exchangers, which comprises dissolving non ionic detergents in the buffered solvents.

US 2005-080000A discloses a method for the chromatographic purification of preproinsulins, in which higher molecular weight substances are removed from an aqueous solution of preproinsulin by a first chromatography on an anion exchanger in flow-through mode and a subsequent second chromatography on a cation exchanger in adsorption mode, and to a method for preparing insulins, which includes the method for preparing preproinsulins.

US 2006-167221A discloses the extraction and isolation of insulins from recombinant sources, particularly those expressed in and secreted by yeasts. Organic solvents have been used to extract host surface bound forms of insulin peptide. In addition, procedures for combining the steps medium clarification, solvent extraction and chromatography, in order to effect the simultaneous isolation and purification of soluble and membrane bound forms of insulin, is disclosed.

U.S. Pat. No. 5,278,284 describes a method of removing a valuable protein from a complex solution and recovering the valuable protein in purified form consists of adding a silica gel sorbant having a pore size approximately the molecular size of the protein to a solution containing the protein, allowing the protein to be sorbed onto the sorbant, separating the sorbant from the solution and then recovering the protein from the sorbant.

U.S. Pat. No. 6,451,987 discloses an ion exchange chromatography process for purifying a peptide from a mixture containing the peptide and related impurities, and to an industrial method including such ion exchange chromatography process.

Some (often related) impurities are often difficult to remove or reduce due to the peak shape, e.g. an impurity eluting in the peak fronting or in the trailing edge. Thus, insufficient purity of a protein of interest may result.

SUMMARY OF THE INVENTION

The present invention provides means for controlling the chromatographic peak shape for improved removal of impurities, e.g. related impurities which are otherwise difficult to remove upon applying a high load of the protein of interest to a column of a chromatographic solid phase material. The peak shape is controlled by means of the presence of di- or polyvalent metal ions in the protein-containing solution applied (i.e. loaded) to the chromatographic column, in combination with adjustment of the pH of the eluent e.g. in view of the isoelectric point (pI) for the protein of interest, and renders it possible to collect a very concentrated pool of the protein of interest in purified form.

It has been found by the present inventor(s) that the controlled peak shape may allow an increased loading of the protein of interest, and thus a higher capacity and fewer runs for a given amount of protein to be purified, just as higher pool concentrations may be obtained.

So, in a first aspect, the present invention relates to a chromatographic process for separating protein components of a protein-containing solution, said solution comprising an insulin peptide and one or more di- or polyvalent metal ions, said insulin peptide being capable of self-association and/or structural change in the presence of di- or polyvalent metal ions, said process comprising the steps of:
  a. applying the protein-containing solution to a column of a chromatographic solid phase material, wherein the loading of the insulin peptide is at least 6.0 g per liter of column volume ($g/L_{CV}$); and
  b. eluting the insulin peptide from said solid phase material by means of an eluent having a pH of at the most 8.5; and collecting a pool of the insulin peptide corresponding to at least 75% by weight of the insulin peptide applied to the column in step (a).

In a second aspect, the present invention relates to a chromatographic process for separating protein components of an insulin-containing solution, said solution comprising an insulin peptide being capable of self-association and/or structural change in the presence of zinc and divalent zinc ions, said process comprising the steps of:
  a. applying the insulin-containing solution to a column of an anion exchange chromatographic solid phase material, wherein the loading of the insulin peptide of interest is at least 6.0 g per liter of column volume ($g/L_{CV}$); and
  b. eluting the insulin peptide of interest from said solid phase material by means of an eluent having a pH of at the most 6.8; and collecting a pool of the insulin peptide of interest corresponding to at least 90% by weight of the insulin peptide of interest applied to the column in step (a).

In a third aspect, the present invention relates to method of controlling peak shape in ion-exchange chromatography of insulin peptides being capable of self-association and/or structural change in the presence of di- or polyvalent metal ions by using
  a. di- or polyvalent metal ions to obtain optimal separation of the insulin peptide and related impurities wherein divalent metal ions have been added to secure a fronting peak shape of the insulin peptide, where the related impurities elutes before the insulin peptide.

BRIEF DESCRIPTION OF THE FIGURES

FIGS. 1-3: Insulin peak profile changing from a tailing peak at high pH (thin dotted curve in FIG. 3, pH=7.2), corresponding to a normal Langmurian profile of somewhat tailing at set point pH (solid thin curve in FIG. 2, pH=6.8), to fronting peak profile at low pH (thick dashed curve I FIG. 1, pH=6.4) by the presence of $Zn^{2+}$ in the mobile phase, i.e. the protein-containing solution.

FIG. 4. Chromatogram of experiment with Zn-balance.

DETAILED DESCRIPTION OF THE INVENTION

As mentioned above, the present invention relates to a chromatographic process for separating protein components of a protein-containing solution. In particular, it is an object to provide an industrially applicable process by which a protein of interest can be separated from related impurities which at the same time obtaining a high recovery of the protein of interest. Such related impurities are typically non-antigenic.

In one aspect is provided a chromatographic process for separating protein components of a protein-containing solution, said solution comprising an insulin peptide and one or more di- or polyvalent metal ions, said insulin peptide being capable of self-association and/or structural change in the presence of di- or polyvalent metal ions, said process comprising the steps of:
  a. applying the protein-containing solution to a column of a chromatographic solid phase material, wherein the loading of the insulin peptide is at least 6.0 g per liter of column volume ($g/L_{CV}$); and
  b. eluting the insulin peptide from said solid phase material by means of an eluent having a pH of at the most 8.5; and collecting a pool of the insulin peptide corresponding to at least 75% by weight of the insulin peptide applied to the column in step (a).

In another aspect is provided a chromatographic process for separating protein components of an insulin-containing solution, said solution comprising an insulin peptide being capable of self-association and/or structural change in the presence of zinc and divalent zinc ions, said process comprising the steps of:
  a. applying the insulin-containing solution to a column of an anion exchange chromatographic solid phase material, wherein the loading of the insulin peptide of interest is at least 6.0 g per liter of column volume ($g/L_{CV}$); and
  b. eluting the insulin peptide of interest from said solid phase material by means of an eluent having a pH of at the most 6.8; and collecting a pool of the insulin peptide of interest corresponding to at least 90% by weight of the insulin peptide of interest applied to the column in step (a).

In another aspect is provided A method of controlling peak shape in ion-exchange chromatography of insulin peptides being capable of self-association and/or structural change in the presence of di- or polyvalent metal ions by using
  a. di- or polyvalent metal ions to obtain optimal separation of the insulin peptide and related impurities wherein divalent metal ions have been added to secure a fronting peak shape of the insulin peptide, where the related impurities elutes before the insulin peptide.

Proteins may originate from yeast expression systems. In the manufacturing process of proteins, the use of chromatographic purification is widespread. The proteins are typically subjected to chemical modifications and a series of chromatographic purification steps, in particular column chromatography including high-performance liquid chromatography (or high-pressure liquid chromatography, HPLC), such as reversed phase chromatography (RPC), hydrophobic interaction chromatography (HIC) and ion exchange chromatography (IEC) (e.g. anion exchange chromatography (AIEC) or cation exchange chromatography (CIEC)), affinity chromatography, size exclusion chromatography, metal-chelate chromatography, pseudo-affinity chromatography, and/or mixed-mode chromatography.

The principle of protein purification using column chromatography is based upon differences in the equilibrium between the stationary and the mobile phase of the proteins to be separated. Using an appropriate combination of stationary and mobile phases, the proteins will leave the column at different intervals. In the context of the present invention, it has been found that modification of the mobile phase initially loaded to the column by means of di- or polyvalent metal ions provides improvements with respect to the control of peak shapes and thereby separation of the protein of interest from closely related impurities.

An important parameter of chromatographic purification is the column capacity, defined by the amount of (target) protein that may be bound to the column. Column capacity is dependent on mobile phase protein concentration, and the depiction of stationary phase protein concentration as a function of mobile phase protein concentration is termed binding isotherms. Binding isotherms may be concave (chromatographic peaks will front) or convex (chromatographic peaks will tail) [J. M. Mollerup, Chem. Eng. Technol. 31 (2008) 864-874]. In rare circumstances, s-shaped isotherms are obtained, where peaks front at low mobile phase concentration and tail at higher mobile phase concentration [J. M. Mollerup et al., J. Liq. Chromatogr. Rel. Technol. 32 (2009) 1577-1597].

Mollerup (J. M. Mollerup, Chem. Eng. Technol. 31 (2008) 864-874) has previously shown that co-operativity where the adsorption of one molecule facilitated the adsorption of another molecule can lead to fronting chromatograms.

In chromatography it is attractive to have a slope up to high concentrations close to the initial slope of the isotherm to obtain a small pool volume and a high pool concentration.

Some relevant parameters are found to be:
Di- or polyvalent metal ions (e.g. $Zn^{2+}$) is trying to make an upward curvature of the isotherm. (dq/dc is increasing—q being the concentration of the protein bound to the solid phase material and c being the concentration of the protein in the solution).
Increased loading on the resin will make a downward curvature (dq/dc is decreasing).
At a pH close to the isoelectric point the net charge is small and the repulsive forces between the proteins are small.
Close to the isoelectric point, the solubility of a protein is normally decreasing. However self-association may lead to an apparent increased solubility around the isoelectric point.

The Protein of Interest

The term "protein" is intended to cover proteins, polypeptides and peptides composed of at least ten constituent amino acid residues connected by peptide bonds. The constituent amino acids may be from the group of the amino acids encoded by the genetic code and they may be natural amino acids which are not encoded by the genetic code, as well as synthetic amino acids.

Herein, the term "amino acid residue" is an amino acid from which, formally, a hydroxy group has been removed from a carboxy group and/or from which, formally, a hydrogen atom has been removed from an amino group.

Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The 22 proteogenic amino acids are: Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, and Valine.

Thus, a non-proteogenic amino acid is a moiety which can be incorporated into a peptide via peptide bonds but is not a proteogenic amino acid. Examples are (but not limited to) γ-carboxyglutamate, ornithine, phosphoserine, the D-amino acids such as D-alanine and D-glutamine. Synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), 3-aminomethyl benzoic acid, anthranilic acid, des-amino-Histidine, the beta analogs of amino acids such as β-alanine etc., D-histidine, desamino-histidine, 2-amino-histidine, β-hydroxy-histidine, homohistidine, $N^{\alpha}$-acetyl-histidine, α-fluoromethyl-histidine, α-methyl-histidine, 3-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid, α-methyl proline, 1-methyl histidine, 3-methyl histidine, and 4,5,6,7-tetrahydro-1H-imidazo[4,5-c]pyridine-6-carboxylic acid β-(1,2,4-triazol-1-yl)-alanine.

When referred to herein, the term "protein of interest" is intended to mean the protein (or proteins) which it is desirable to obtain in an isolated, concentrated or purified form compared to the protein present in the protein-containing solution (see below). In some instances, the protein of interest may undergo certain well-defined changes in the course of the chromatographic process; it is of course to be understood that in such instances the protein of interest in the protein-containing solution and in the resulting form may not be chemically or structurally identical.

It is believed that the chromatographic process is particularly suited for proteins which are capable of self-association and/or structural change in the presence of di- or polyvalent metal ions. Examples of such proteins are insulin peptides, glucagon-like peptides, exendins, glucagon, hGH, aprotinin, insulin-like growth factor-1, insulin-like growth factor-2, gastric inhibitory peptide, growth hormone-releasing factor, pituitary adenylate cyclase activating peptides, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods, GIP, peptide histidine-methionine amide, helospectins, helodermin, pituitary adenylate cyclase activating peptide-related peptide, vasoactive intestinal polypeptide, including variants thereof (cf. below).

The currently most interesting proteins of interest are those selected from insulin peptides, glucagon-like peptides, and exendins, including variants thereof.

In some particularly interesting embodiments, the protein of interest is selected from insulin polypeptides, including variants thereof.

A particularly interesting group of proteins is the one represented by those being capable of self-association in the presence of divalent metal ions, such as $Zn^{2+}$.

The term "variant" as used herein in relation to a protein means a modified protein which is an analog of the parent protein, a derivative of the parent protein (including DPP-IV protected forms) or a derivative of an analog of the parent protein (including DPP-IV protected forms).

The term "analogue" as used herein referring to a protein means a modified protein wherein one or more amino acid residues of the protein have been substituted by other amino acid residues and/or wherein one or more amino acid residues have been deleted from the protein and/or wherein one or more amino acid residues have been deleted from the protein and or wherein one or more amino acid residues have been added to the protein. Such addition or deletion of amino acid residues can take place at the N-terminal of the protein and/or at the C-terminal of the protein. Two different and simple systems are often used to describe analogues: For example Arg$^{34}$-GLP-1(7-37) or K34R-GLP-1(7-37) designates a GLP-1 analogue wherein the naturally occurring lysine at position 34 has been substituted with arginine (standard single letter abbreviation for amino acids used according to IUPAC-IUB nomenclature).

The term "derivative" as used herein in relation to a parent protein means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, pegylations and the like. An examples of a derivative of GLP-1(7-37) is Arg$^{34}$, Lys$^{26}$(N$^{\epsilon}$-(γ-Glu(N$^{\alpha}$-hexadecanoyl)))-GLP-1(7-37). Derivatives also include DPP-IV protected forms of the protein in question.

The term "DPP-IV protected" as used herein referring to a protein means a protein which has been chemically modified in order to render said compound resistant to the plasma peptidase dipeptidyl aminopeptidase-4 (DPP-IV). The DPP-IV enzyme in plasma is known to be involved in the degradation of several proteins (such as peptide hormones), e.g. GLP-1, GLP-2, Exendin-4 etc. Thus, a considerable effort is being made to develop analogues and derivatives of the protein susceptible to DPP-IV mediated hydrolysis in order to reduce the rate of degradation by DPP-IV. In one embodiment a DPP-IV protected protein is more resistant to DPP-IV than GLP-1(7-37) or Exendin-4(1-39).

The term "human insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

"An insulin" is herein to be understood as human insulin or an insulin from another species such as porcine or bovine insulin.

The term "insulin peptide" as used herein means a peptide (protein) which is either an insulin or an analog or a derivative thereof with insulin activity, i.e. it activates the insulin receptor.

The term "insulin analogue" as used herein means a modified insulin wherein one or more amino acid residues of the insulin have been substituted by other amino acid residues and/or wherein one or more amino acid residues have been deleted from the insulin and/or wherein one or more amino acid residues have been added and/or inserted to the insulin. The amino acids are, preferably, amino acids which can be coded for by a triplet ("codon") of nucleotides, vide genetic engineering. Herein, amino acids can be given by their common three letter codes, preferably: Gly, Pro, Ala, Val, Leu, Ile, Met, Cys, Phe, Tyr, Trp, His, Lys, Arg, Gln, Asn, Glu, Asp, Ser and Thr. Alternatively, the one letter codes can be used.

In one embodiment an insulin analogue comprises less than 8 modifications (substitutions, deletions, additions (including insertions) and any combination thereof) relative to the parent insulin, alternatively less than 7 modifications relative to the parent insulin, alternatively less than 6 modifications relative to the parent insulin, alternatively less than 5 modifications relative to the parent insulin, alternatively less than 4 modifications relative to the parent insulin, alternatively less than 3 modifications relative to the parent insulin, alternatively less than 2 modifications relative to the parent insulin.

Modifications in the insulin molecule are denoted stating the chain (A or B), the position, and the one or three letter code for the amino acid residue substituting the native amino acid residue.

By "connecting peptide" or "C-peptide" is meant a connection moiety "C" of the B-C-A polypeptide sequence of a single chain proinsulin-molecule. In the human insulin chain, the C-peptide connects position 30 of the B chain and position 1 of the A chain and is 35 amino acid residue long. The connecting peptide includes two terminal dibasic amino acid sequence, e.g., Arg-Arg and Lys-Arg which serve as cleavage sites for cleavage off of the connecting peptide from the A and B chains to form the two-chain insulin molecule.

By "desB30" or "B(1-29)" is meant a natural insulin B chain or an analogue thereof lacking the B30 amino acid and "A(1-21)" means the natural insulin A chain. Thus, e.g., A21Gly,B28Asp,desB30 human insulin is an analogue of human insulin where the amino acid in position 21 in the A chain is substituted with glycine, the amino acid in position 28 in the B chain is substituted with aspartic acid, and the amino acid in position 30 in the B chain is deleted.

Herein terms like "A1", "A2" and "A3" etc. indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21Gly and A21Gln, respectively.

Herein the terms "A(0)" or "B(0)" indicate the positions of the amino acids N-terminally to A1 or B1, respectively. The terms A(−1) or B(−1) indicate the positions of the first amino acids N-terminally to A(0) or B(0), respectively. Thus A(−2) and B(−2) indicate positions of the amino acids N-terminally to A(−1) and B(−1), respectively, A(−3) and B(−3) indicate positions of the amino acids N-terminally to A(−2) and B(−2), respectively, and so forth.

Herein the terms A(0) or B(0) indicate the positions of the amino acids N-terminally to A1 or B1, respectively. The terms A(−1) or B(−1) indicate the positions of the first amino acids N-terminally to A(0) or B(0), respectively. Thus A(−2) and B(−2) indicate positions of the amino acids N-terminally to A(−1) and B(−1), respectively, A(−3) and B(−3) indicate positions of the amino acids N-terminally to A(−2) and B(−2), respectively, and so forth. The terms A22 or B31 indicate the positions of the amino acids C-terminally to A21 or B30, respectively. The terms A23 or B32 indicate the positions of the first amino acids C-terminally to A22 or B31, respectively. Thus A24 and B33 indicate positions of the amino acids C-terminally to A23 and B32, respectively, and so forth.

Examples of insulin analogues are such wherein Pro in position 28 of the B chain is substituted with Asp, Lys, Leu, Val, or Ala and/or Lys at position B29 is substituted with Pro, Glu or Asp. Furthermore, Asn at position B3 may be substituted with Thr, Lys, Gln, Glu or Asp. The amino acid residue in position A21 may be substituted with Gly. Also one or more amino acids may be added to the C-terminal of the A-chain and/or B-chain such as, e.g., Lys. The amino acid in position B1 may be substituted with Glu. The amino acid in position B16 may be substituted with Glu or His. Further examples of insulin analogues are the deletion analogues, e.g., analogues where the B30 amino acid in human insulin has been deleted (des(B30) human insulin), insulin analogues wherein the B1 amino acid in human insulin has been deleted (des(B1) human insulin), des(B28-B30) human insulin and des(B27) human insulin. Insulin analogues wherein the A-chain and/or the B-chain have an N-terminal extension and insulin analogues wherein the A-chain and/or the B-chain have a C-terminal extension such as with two arginine residues added to the C-terminal of the B-chain are also examples of insulin analogues. Further examples are insulin analogues comprising combinations of the mentioned mutations. Insulin analogues wherein the amino acid in position A14 is Asn, Gln, Glu, Arg, Asp, Gly or His, the amino acid in position B25 is His and which optionally further comprises one or more additional mutations are further examples of insulin analogues. Insulin analogues of human insulin wherein the amino acid residue in position A21 is Gly and wherein the insulin analogue is further extended in the C-terminal with two arginine residues are also examples of insulin analogues.

Further examples of insulin analogues include: DesB30 human insulin; AspB28 human insulin; AspB28,desB30 human insulin; LysB3,GluB29 human insulin; LysB28, ProB29 human insulin; GlyA21,ArgB31,ArgB32 human insulin; GluA14,HisB25 human insulin; HisA14,HisB25 human insulin; GluA14,HisB25,desB30 human insulin; HisA14, HisB25,desB30 human insulin; GluA14,HisB25, desB27,desB28,desB29,desB30 human insulin; GluA14, HisB25,GluB27,desB30 human insulin; GluA14,HisB16, HisB25,desB30 human insulin; HisA14,HisB16,HisB25, desB30 human insulin; HisA8,GluA14,HisB25,GluB27, desB30 human insulin; HisA8,GluA14,GluB1,GluB16, HisB25,GluB27,desB30 human insulin; and HisA8, GluA14,GluB16,HisB25,desB30 human insulin.

The term "insulin derivative" as used herein means a chemically modified parent insulin or an analogue thereof, wherein the modification(s) are in the form of attachment of amides, carbohydrates, alkyl groups, acyl groups, esters, PEGylations, and the like. Examples of derivatives of human insulin are human insulin B30 threonine methyl ester, GlyA21,ArgB31,Arg-amideB32 human insulin, $N^{\epsilon B29}$-tetradecanoyl desB30 human insulin, $N^{\epsilon B29}$-tetradecanoyl human insulin, $N^{\epsilon B29}$-decanoyl desB30 human insulin, $N^{\epsilon B29}$-dodecanoyl desB30 human insulin, $N^{\epsilon B29}$-3-(2-{2-(2-methoxy-ethoxy)-ethoxy}ethoxy)-propionyl human insulin, LysB29(Nε-hexadecandioyl-γ-Glu) des(B30) human insulin); $N^{\epsilon B29}$-(N$^\alpha$-(Sar-OC(CH$_2$)$_{13}$CO)-γ-Glu) desB30 human insulin, $N^{\epsilon B29}$-ω-carboxy-pentadecanoyl-γ-L-glutamylamide desB30 human insulin, $N^{\epsilon B29}$-hexadecan-dioyl-γ-amino-butanoyl desB30 human insulin, $N^{\epsilon B29}$-hexadecandioyl-γ-L-Glu-amide desB30 insulin.

The term "glucagon-like peptide" as used herein refers to the homologous peptides glucagon-like peptide 1 (GLP-1), glucagon-like peptide 2 (GLP-2), and oxynthomodulin (OXM) derived from the preproglucagon gene, the exendins, as well as analogues and derivatives thereof. The exendins which are found in the Gila monster are homologous to GLP-1 and also exert an insulinotropic effect. Examples of exendins are exendin-4 and exendin-3.

The term "GLP-1 peptide", as used herein, is intended to designate GLP-1 (7-37), GLP-1 (7-36) amide as well as analogues and derivatives thereof, which are capable of being produced by conventional recombinant DNA techniques as well as conventional synthetic methods. Such GLP-1 peptides include but are not limited to native glucagon-like peptide-1, for instance such peptide fragments which comprises GLP-1 (7-37) and functional derivatives thereof as disclosed in WO 87/06941; such peptide fragments which comprise GLP-1 (7-36) and functional derivatives thereof as disclosed in WO 90/11296; such analogues of the active GLP-1 peptides 7-34, 7-35, 7-36, and 7-37 as disclosed in WO 91/11457; such GLP-1 derivatives in which a lipophilic substituent is attached to at least one amino acid residue as disclosed in WO 98/08871; such N-terminal truncated fragments of GLP-1 as disclosed in EP 0699686-A2; and such GLP-1 analogues and derivatives that include an N-terminal imidazole group as disclosed in EP 0708179-A2.

The term "GLP-2 peptide", as used herein, is intended to designate GLP-2 (1-35), GLP-2 (1-34), GLP-2 (1-33) as well as analogues and derivatives thereof, which are capable of being produced by conventional recombinant DNA techniques as well as conventional synthetic methods. Such GLP-2 peptides include but are not limited to native glucagon-like peptide-2, GLP-2 derivatives in which a lipophilic substituent is attached to at least one amino acid residue as disclosed in WO 98/08872, human glucagon-like peptide-2 (hGLP-2), GLP-2(1-30); GLP-2(1-31); GLP-2(1-32); GLP-2(1-33); GLP-2(1-34), GLP-2(1-35), Lys$^{20}$GLP-2(1-33), Lys$^{20}$Arg$^{30}$GLP-2(1-33), Arg$^{30}$Lys$^{34}$GLP-2(1-34), Arg$^{30}$Lys$^{35}$GLP-2(1-35), Arg$^{30,35}$Lys$^{20}$GLP-2(1-35), Arg$^{35}$GLP-2(1-35), Lys$^{20}$(N$^\epsilon$-tetradecanoyl)GLP-2(1-33); Lys$^{20,30}$-bis(N$^\epsilon$-tetradecanoyl)-GLP-2(1-33); Lys$^{20}$(N$^\epsilon$-tetradecanoyl)Arg$^{30}$GLP-2(1-33); Arg$^{30}$Lys$^{35}$(N$^\epsilon$-tetradecanoyl)GLP-2(1-35); Arg$^{30,35}$Lys$^{20}$(N$^\epsilon$-tetradecanoyl)GLP-2(1-35); Arg$^{35}$Lys$^{30}$(N$^\epsilon$-tetradecanoyl)GLP-2(1-35); Arg$^{30}$Lys$^{34}$(N$^\epsilon$-tetradecanoyl)GLP-2(1-34); Lys$^{20}$(N$^\epsilon$-(ω-carboxynonadecanoyl))GLP-2(1-33); Lys$^{20,30}$-bis(N$^\epsilon$-(∩-carboxynonadecanoyl))GLP-2(1-33); Lys$^{20}$(N$^\epsilon$-(∩-carboxynonadecanoyl))-Arg$^{30}$GLP-2(1-33); Arg$^{30}$Lys$^{35}$(N$^\epsilon$-(∩-carboxynonadecanoyl))GLP-2(1-35); Lys$^{30}$(N$^\epsilon$-(γ-glutamyl(N$^\alpha$-tetradecanoyl)))hGLP-2, Lys$^{30}$(N$^\epsilon$-(γ-glutamyl(N$^\alpha$-hexadecanoyl)))hGLP-2, Arg$^{30,35}$Lys$^{20}$(N$^\epsilon$-(∩-carboxynonadecanoyl))GLP-2(1-35); Arg$^{35}$Lys$^{30}$(N$^\epsilon$-(∩-carboxynonadecanoyl))GLP-2(1-35); and Arg$^{30}$Lys$^{34}$(N$^\epsilon$-(∩-carboxynonadecanoyl))GLP-2(1-34).

The term "exendin" as used herein, is intended to designate exendin as well as analogs, derivatives, and fragments thereof, e.g. exendin-3 and -4. Exendin as well as analogs, derivatives, and fragments thereof are described in, for example WO 99/43708, the contents of which are herein incorporated by reference in their entirety.

One aim of the present invention is to provide a method for removing one or more related impurities in view of the protein of interest.

The term "related impurity" as used herein means an impurity which has structural resemblance to the protein of interest. A related impurity has different chemical or physical structure than the protein of interest, for instance a truncated form, an extended form (extra amino acids, various derivatives etc.), a deamidated form, an incorrectly folded form, a form with undesired (e.g. excess, incorrect or insufficient) glycosylation including sialylation, oxidated forms, forms resulting from racemization, forms wherein an acylation has taken place on another residue than desired, and others.

In one embodiment, such related impurities elute before the protein of interest.

It follows then that the term "unrelated impurities" as used herein, is intended to cover impurities which are different from related impurities.

In contrast to related impurities, unrelated impurities may be antigenic.

The Protein-Containing Solution

The starting material for the chromatographic process may be any protein-containing solution comprising the protein of interest, such as a protein selected from insulin peptides, glucagon-like peptides, and exendins, including variants thereof (see above). The starting material may be the medium obtained from yeast expression systems directly or chemical synthesis directly, or the starting material may have been subjected to several purification or chemical modification steps prior to the process according to the invention.

In some interesting embodiments, the protein-containing solution comprises one or more di- or polyvalent metal ions. Without being bound by any particular theory, it is currently believed that such di- or polyvalent metal ions facilitate self-association and/or structural changes of the protein of interest whereby the peak shape in the chromatographic process will be modified so that closely related impurities, in particular those eluting before the protein of interest, can be separated from the protein of interest.

A distinctive property of insulin is its ability to associate into hexamers, in which form the hormone is protected from chemical and physical degradation during biosynthesis and storage. X-ray crystallographic studies on insulin show that the hexamer consists of three dimers related by a 3-fold axis of rotation. These dimers are closely associated through the interaction of two zinc ions at its core positioned on the 3-fold axis.

Suitable examples of di- or polyvalent metal ions, including transition metal ions, are those are selected from $Zn^{2+}$, $Ca^{2+}$, $Mg^{2+}$, $Ni^{2+}$, $Cu^{2+}$, $Ba^{2+}$, preferably $Zn^{2+}$. Two or more types of the di- or polyvalent metal ions may be present in the protein-containing solution, or just one type.

The concentration of the di- or polyvalent metal ions in the protein-containing solution is typically in the range of 0.01-200 mM, such as 0.1-100 mM, e.g. 0.5-75 mM.

The ratio between the charge equivalents of the di- or polyvalent metal ions and the protein of interest (i.e. the equivalent charge per molecule of the protein of interest) is typically from 0.1:1 to 50:1, such as from 0.3:1 to 20:1, e.g. from 0.4:1 to 15:1, or from 0.5:1 to 10:1.

In the instances where the protein of interest is an insulin peptide, the ratio between the charge equivalents of the di- or polyvalent metal ions, e.g. $Zn^{2+}$ ions, and the insulin peptide is typically from 1:6 to 20:6, such as from 2:6 to 15:6, e.g. from 3:6 to 10:6, or from 3:6 to 5:6, or from 7:6 to 9:6. As an illustrative example, two zinc ions per molecule of insulin is understood as a ratio between the charge equivalents of the di- or polyvalent metal ions ($Zn^{2+}$) and insulin of 4:1 (i.e. (2 zinc*2 charges per zinc):1). In the presence of $Zn^{2+}$, insulin is able to self-associate by forming hexamers, di-hexamers or even larger complexes of insulin peptide, which are still soluble. which are utilised in the crystallisation of insulin. Hence, in some embodiments, the protein-containing solution is obtained from an insulin peptide crystallized with zinc.

It may further be desirable or necessary to adjust the concentration of any solvents or to reduce the ion strength by adding water to the protein-containing solution. The pH may be adjusted by means of a suitable buffer, and a solvent, e.g. ethanol, may be added in order to increase the solubility of the protein of interest. Hence, the protein-containing solution may also comprise solvents, salts, buffers, modifiers/excipients (organic or inorganic). The organic solvent could be but is not limited to any monohydric aliphatic alcohol (methanol, ethanol, propanols and butanols), e.g methanol, ethanol, 2-propanol, 1-propanol and hexylene glycol. Optional salt components for any section of the chromatographic purification may be any salt including but not limited to: NaCl, KCl, $NH_4Cl$, sodium acetate, potassium acetate, ammonium acetate, etc. Any buffer component can be used including but not limited to: Citrate buffers, phosphate buffers, TRIS buffers, borate buffers, carbonate buffers, acetate buffers, ammonium buffers, glycine buffers etc. In one embodiment, the solvent is pH-buffered in the range from pH 5 to pH 9.

The ionic strength indicated as the conductivity at 25° C. of the protein-containing solution may also play a role. Hence, in some embodiments, the conductivity of the protein-containing solution is in the range of 0-100 mS/cm, such as 0-50 mS/cm, e.g. 0-30 mS/cm, or 0.01-100 mS/cm, such as 0.05-50 mS, e.g. 0.1-30 mS/cm.

The pH of the protein-containing solution is typically kept in the range of 0-14, 1-13, 2-12, 3-11, or 4-10. In many instances, however, the pH of the protein-containing solution is about the same as the pH of the eluent.

The Chromatographic Process

The aim of the chromatographic process is to separate the protein of interest from other constituents of the protein-containing solution, or to obtain the protein of interest in a higher degree of purity, or at least to reduce the presence of one or more impurities relative to the protein of interest.

The chromatographic process will be described in details in the following.

Step (a)

In the first step of the process according to the invention, the protein-containing solution is applied to a column of the chromatographic solid phase material.

The solid phase material is selected in accordance with the type of chromatographic process, e.g. reversed-phase chromatography (RPC), ion-exchange chromatography (IEC), such as anion-exchange chromatography (AIEC) or cation-exchange chromatography (CIEC), hydrophobic interaction chromatography (HIC), affinity chromatography, size exclusion chromatography, metal-chelate chromatography, pseudo-affinity chromatography, mixed-mode chromatography, etc. Hence, the solid phase material may be selected from an ion exchange chromatographic material (IEC), a reverse-phase chromatographic material (RPC), a hydrophobic-interaction chromatographic material (HIC), etc. Preferably ion exchange chromatographic material is used, in particular an anion exchange chromatographic material.

Insofar an ion-exchange chromatographic process is desirable, the solid phase material may be selected depending on the specific peptide to be purified and the conditions employed, such as pH, buffer, ionic strength, etc., which are known to the person skilled in the art (that is, typically, pH below the isoelectric point (pI) of the peptide for cation exchange resins and pH above pI of the peptide for anion exchange resins, a sufficient buffer strength to maintain the desired pH, and a sufficiently low ionic strength possibly induced by the salt concentration). Non-limiting examples of suitable solid phase materials are Sepharose resins, Sephadex resins, Streamline resins, and Source resins from Amersham-Pharmacia Biotech, HyperD resins, Trisacryl resins, and Spherosil resins from BioSepra, TSKgel resins and Toyopearl resins from TosoHaas, Fractogel EMD resins from Merck, Poros resins from Perseptive Biosystems, Macro-Prep resins from BioRAD, Express-ion resins from Whatman etc.

For a reversed phase chromatographic process the solid phase material may be any choice of chromatographic reversed phase resin optionally with any kind of substitution, including but not limited to: silica based resins, such as Kromasil 100 $C_{18}$, polymer based resins such as Source from Amersham Biosciences, Poros materials from Applied Biosystems, e.g. Poros R1, R2 and R3 reversed phase resins, ceramic based resins from Ciphergen, metal oxide based resins, and others. Preferably, a silica based resin is used. The equilibration solution (solution for equilibrating the solid phase materials before step (a)) and the protein-containing solution for application may or may not contain an organic solvent. The organic solvent could be but is not limited to any monohydric aliphatic alcohol (methanol, ethanol, propanols and butanols), e.g methanol, ethanol, 2-propanol, 1-propanol and hexylene glycol. Optional salt components for any section of the chromatographic purification may be any salt including but not limited to: NaCl, KCl, $NH_4Cl$, $CaCl_2$, sodium acetate, potassium acetate, ammonium acetate etc. Any buffer component can be used including but not limited to: Citrate buffers, phosphate buffers, TRIS buffers, borate buffers, carbonate buffers, acetate buffers, ammonium buffers, glycine buffers etc. In one embodiment, the solvent is pH-buffered in the range from pH 5 to pH 9.

In one embodiment, a reversed phase high performance liquid chromatographic process is performed using a silica based chromatographic resin, e.g. a substituted silica gel, such as $C_4$-, $C_6$-, $C_8$-, $C_{12}$-, $C_{16}$-, $C_{18}$-, $C_{20}$-, phenyl- or benzene-substituted silica gel. In another embodiment, a reversed phase high performance liquid chromatographic process is performed using a chromatographic resin which is a polymeric base material.

For hydrophobic interaction chromatography, solid phase material is a matrix substituted with hydrophobic ligands such as ethyl, butyl, phenyl or hexyl (which appears to be responsible for binding the protein). Preferred materials are those substituted with butyl and/or phenyl ligands.

The solid phase material used is most often presented in the form of beads, e.g. a particulate material having an average diameter of in the range of 0.1-1000 µm, e.g. in the range of 1-100 µm. The solid phase material is suitably arranged in a HPLC column arranged with pumps, etc. as it will be evident for the skilled person.

The application of the protein-containing solution to the column of the chromatographic solid phase material is typically conducted according to conventional protocols, i.e. the concentration, temperature, ionic strength, etc. of the protein-containing solution may be as usual (with the modifications suggested herein), and the hydrophobic interaction chromatography material may be washed and equilibrated before application as usual.

It has been found that the loading of the protein of interest may be fairly high, e.g. at least 6.0 g of the protein of interest per liter of column volume ($g/L_{CV}$), and due to the improved peak shape in the process, the pool volume will be somewhat reduced compared to conventional processes. In some embodiments, the loading of the protein of interest is at least 7.0 $g/L_{CV}$, or at least 8.0 $g/L_{CV}$, or at least 8.5 $g/L_{CV}$, or 6.0-50 $g/L_{CV}$, or 7.0-40 $g/L_{CV}$, or 8.0-30 $g/L_{CV}$, such as 8.5-25 $g/L_{CV}$, such as 9.0-20 $g/L_{CV}$, or 9.5-15 $g/L_{CV}$. The loading of the protein of interest may at maximum be loaded up to the capacity of the column. The column volume typically corresponds to the volume of the packed swollen chromatographic solid phase material.

Although not limited thereto, the process of the present invention is particularly feasible for "large-scale" (or "industrial-scale") purposes. Hence, in some important embodiments, the process is a large-scale process wherein the column volume is at least 1 L, or at least 10 L, or at least 20 L, or at least 50 L, or at least 100 L, such as at least 500 L, e.g. at least 1000 L, or at least 5000 L.

Although not particularly critical, it may be desirable to adjust the temperature of the column and the protein-containing solution so as to further improve the peak shape. Typically, the temperature is 0-70° C., 0-50° C., such as 2-30° C. The temperature of the column may be kept within a specified range by using a cooling jacket and solutions of controlled temperature.

Step (b)

In the second step of the process, which typically is conducted without interruption of the overall process, the protein of interest is eluted from the solid phase material by means of an eluent.

The typical principle of elution in ion-exchange chromatography in industrial purification processes is salt component gradients in an aqueous buffer solution at constant pH, either as step or linear gradients. Isocratic elution is also possible. Organic solvents or modifiers may be added to the eluent to keep the protein on the desired form or just in solution. Also, a change in pH may occasionally be employed to elute the protein of interest.

For a hydrophobic interaction chromatography process, the type of elution is not particularly critical, thus, it is, e.g., possible to elute with a elution buffer comprising a stepwise decreasing gradient of a salt and/or zwitterion, elute with a linear decreasing gradient of a salt (or a gradient-hold-gradient profile, or other variants), or to use a pH gradient, or to us a temperature gradient, or a combination of the before-mentioned. Alternatively, a gradient of a calcium chelating compound (e.g. EDTA, citrate, malonate, etc.) or a solvent less polar than water (e.g. aqueous solutions comprising ethanol, PEG, 2-propanol, or the like), may be used as the elution buffer. In one embodiment, the elution buffer comprises a salt in an initial concentration of in the range of 0.7-2.2 M. Hence, in one embodiment, the elution buffer is a gradient buffer with respect to the an ammonium salt, wherein the initial concentration of the ammonium salt of the gradient buffer is in the range of 1.7-2.2 M, and the final concentration of the ammonium salt of the gradient buffer is in the range of 0.0-1.6 M. The conductivity of the final elution buffer is preferably lower than the conductivity of the protein-containing solution in step (a). In many instances, the elution buffer in step (b) has a pH as in step (a).

For a reversed phase high performance liquid chromatographic process, the solvent used for elution is typically pH-buffered in the range from pH 4 to pH 10. The eluent may comprise an alcohol in a concentration from 10% w/w to 80% w/w. The protein of interest and impurities may be eluted and separated by a step, asymptotic or linear change gradient or isocratically in organic solvent, or in combinations of these. The organic solvent component gradient would be from a lower to a higher concentration. Elution may also be possible by changing pH and/or temperature in the elution section.

The choice of starting pH, buffer and ionic strength is done according to well-known techniques such as conventional test-tube methods, cf. e.g. handbooks from Amersham-Pharmacia Biotech, or Fundamentals of preparative and nonlinear chromatography, Georges Guiochon, Dean G. Shirazi, Attila Felinger, Anita M. Katti, Academic Press, 2006.

In one embodiment, the eluent comprises a salt component selected from any organic or inorganic salt, preferably from NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof, most preferred sodium acetate, potassium acetate, ammonium acetate, NaCl, $NH_4Cl$, KCl.

The salt component is typically present in a concentration of from 0.1 mM to 3000 mM, preferably from 1 mM to 1000 mM, more preferably from 5 mM to 500, most preferably from 20 mM to 300 mM.

The eluent may also comprise a buffer, e.g., selected from citrate buffers, phosphate buffers, tris buffers, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, tri-ethanol amine, imidazole buffers, pyridine buffers and barbiturate buffers and mixtures thereof, preferably citric acid, sodium citrate, sodium phosphate, phosphoric acid, glutamic acid, sodium glutamate, glycin, sodium carbonate, potassium citrate, potassium phosphate, potassium glutamate, potassium carbonate, tris-hydroxymethyl amino methane and boric acid and mixtures thereof.

The buffer is typically present in a concentration of from 0.1 mM to 500 mM, preferably from 1 mM to 200 mM, more preferably from 5 mM to 100 mM, most preferably from 10 mM to 50 mM.

The pH of the eluent is typically at the most 8.5, such as at the most 8.0, or at the most 7.5, or at the most 7.0, or at the most 6.9, or at least 6.8, or at least 6.7, or at least 6.6, or at least 6.5, e.g. in the range of 4.5-8.5, or 4.5-8.0, or 4.5-7.5, or 4.5-7.0, such as 4.6-8.0, or 4.6-7.5, or 4.6-7.0, or 4.6-6.9, or 4.7-7.5, or 4.7-7.0, or 4.7-6.7, or 4.8-7.5, or 4.8-7.0, or 4.8-6.6, or 4.9-6.5, or 5.0-6.4.

It has been found that the process may be even further improved if the pH of the eluent is at the most 2.1 units higher than the pI of the protein of interest, e.g. at the most 1.9 units higher, such as at the most 1.7 units higher.

The term "pI" or "isoelectric point" as used herein means the pH value where the overall net charge of the protein is zero.

In some embodiments, the eluent may also comprise one or more di- or polyvalent metal ions, such as those mentioned further above for the protein-containing solution.

Without being bound by any particular theory, it is currently believed that the presence of such di- or polyvalent metal ions in the eluent preserves the self-association and/or structural changes of the protein of interest induced in step (a) whereby the peak shape in the chromatographic process will be modified so that closely related impurities, in particular those eluting before the protein of interest, can be separated from the protein of interest.

Suitable examples of di- or polyvalent metal ions, including transition metal ions, are those are selected from $Zn^{2+}$, $Ca^{2+}$, $Mg^{2+}$, $Ni^{2+}$, $Cu^{2+}$, $Ba^{2+}$, preferably $Zn^{2+}$. Two or more types of the di- or polyvalent metal ions may be present in the eluent, or just one type.

When present, the concentration of the di- or polyvalent metal ions in the eluent is preferably in the range of 0.1-200 mM, such as 0.5-100 mM, or 1.0-60 mM.

In one particular embodiment, the eluent comprises $Zn^{2+}$ ions, e.g. in concentrations in the range of 0.01-200 mM, such as 0.1-100 mM, e.g. 0.5-75 mM.

The ratio between the charge equivalents of the di- or polyvalent metal ions in the eluent and the protein of interest (i.e. the equivalent charge per molecule of the protein of interest) is typically from 0.1:1 to 50:1, such as from 0.3:1 to 20:1, e.g. from 0.4:1 to 15:1, or from 0.5:1 to 10:1.

In the instances where the protein of interest is an insulin peptide, the ratio between the charge equivalents of the di- or polyvalent metal ions in the eluent, e.g. $Zn^{2+}$ ions, and the insulin peptide is typically from 1:6 to 20:6, such as from 2:6 to 15:6, e.g. from 3:6 to 10:6, or from 3:6 to 5:6, or from 7:6 to 9:6.

In connection with the elution, the protein of interest is collected. Hence, it is an feature of the invention to collecting a pool of the protein of interest corresponding to at least 75% by weight of the protein of interest applied to the column in step (a). In some embodiments, the pool of the protein of interest collected in step (b) corresponds to at least 80% by weight, such as at least 85% by weight, or at least 90% by weight, or at least 91% by weight, or at least 92% by weight, or at least 93% by weight, or at least 94% by weight, or at least 95% by weight, or at least 96% by weight, of the protein of interest applied to the column in step (a).

By means of process of the present invention, it is desirable to exclude from the pool of the protein of interest any closely related proteins.

It should be understood that it may be desirable to include a washing step after step (a), but before step (b) using a washing buffer prior to the elution step (step (b)). The washing buffer is typically an aqueous solution comprising a buffering agent, typically a buffering agent comprising at least one component selected from the groups consisting of acids and salts of MES, PIPES, ACES, BES, TES, HEPES, TRIS, histidine, imidazole, glycine, glycylglycine, glycinamide, phosphoric acid, acetic acid (e.g. sodium acetate), lactic acid, glutaric acid, citric acid, tartaric acid, malic acid, maleic acid, and succinic acid. It should be understood that the buffering agent may comprise a mixture of two or more components, wherein the mixture is able to provide a pH value in the specified range. As examples can be mentioned acetic acid and sodium acetate, etc. It should further be understood that the washing step (b) may be conducted by using one, two or several different washing buffers, or by the application of a gradient washing buffer. It should also be noted that the washing step and the elution step need not to be discrete steps, but may be combined, in particular if a gradient elution buffer is utilised in the elution step.

The product obtained from the process of the invention (steps (a) and (b)) may if desirable undergo further conventional purification and isolation steps.

Currently Preferred Embodiment of the Invention

In one currently preferred embodiment, the invention provides a chromatographic process for separating protein components of an insulin-containing solution, said solution comprising an insulin peptide being capable of self-association and/or structural change in the presence of zinc and divalent zinc ions, said process comprising the steps of:

a. applying the insulin-containing solution to a column of an anion exchange chromatographic solid phase material, wherein the loading of the insulin peptide of interest is at least 6.0 g per liter of column volume (g/$L_{CV}$); and b. eluting the insulin peptide of interest from said solid phase material by means of an eluent having a pH of at the most 6.8; and collecting a pool of the insulin peptide of interest corresponding to at least 90% by weight of the insulin peptide of interest applied to the In one embodiment of the above, the ratio between the charge equivalents of the di- or polyvalent metal ions, e.g. $Zn^{2+}$ ions, and the insulin peptide is typically from 1:6 to 20:6, such as from 2:6 to 15:6, e.g. from 3:6 to 10:6, or from 3:6 to 5:6, or from 7:6 to 9:6.

The invention is summarized in the following paragraphs:

1. A chromatographic process for separating protein components of a protein-containing solution, said solution comprising an insulin peptide and one or more di- or polyvalent metal ions, said insulin peptide being capable of self-association and/or structural change in the presence of di- or polyvalent metal ions, said process comprising the steps of:
  a. applying the protein-containing solution to a column of a chromatographic solid phase material, wherein the loading of the insulin peptide is at least 6.0 g per liter of column volume (g/$L_{CV}$); and
  b. eluting the insulin peptide from said solid phase material by means of an eluent having a pH of at the most 8.5; and collecting a pool of the insulin peptide corresponding to at least 75% by weight of the insulin peptide applied to the column in step (a).

2. The process according paragraph 1, wherein the di- or polyvalent metal ions are selected from $Zn^{2+}$, $Ca^{2+}$, $Mg^{2+}$, $Ni^{2+}$, $Cu^{2+}$, $Ba^{2+}$, preferably $Zn^{2+}$.

3. The process according to any one of the preceding paragraphs, wherein the concentration of the di- or polyvalent metal ions in the solution is in the range of 0.01-200 mM, such as 0.1-100 mM, e.g. 0.5-75 mM.

4. The process according to any one of the preceding paragraphs, wherein the ratio between the charge equivalents of the di- or polyvalent metal ions and the insulin peptide is typically from 0.1:1 to 50:1, such as from 0.3:1 to 20:1, e.g. from 0.4:1 to 15:1, or from 0.5:1 to 10:1.

5. The process according to any one of the preceding paragraphs, wherein the conductivity of the protein-containing solution is in the range of 0-100 mS/cm, such as 0-50 mS/cm, e.g. 0-30 mS/cm, or 0.01-100 mS/cm, such as 0.05-50 mS, e.g. 0.1-30 mS/cm.

6. The process according to any one of the preceding paragraphs, wherein the solid phase material is selected from an ion exchange chromatographic material (IEC), a reverse-phase chromatographic material (RPC), a hydrophobic-interaction chromatographic material (HIC), such as an ion exchange chromatographic material, in particular an anion exchange chromatographic material.

7. The process according to any one of the preceding paragraphs, wherein the loading of the insulin peptide is at least 7.0 g/$L_{CV}$, or at least 8.0 g/$L_{CV}$, or at least 8.5 g/$L_{CV}$, or 6.0-50 g/$L_{CV}$, or 7.0-40 g/$L_{CV}$, or 8.0-30 g/$L_{CV}$, such as 8.5-25 g/$L_{CV}$, such as 9.0-20 g/$L_{CV}$, or 9.5-15 g/$L_{CV}$.

8. The process according to any one of the preceding paragraphs, wherein the pH of the eluent is at the most 8.5, such as at the most 8.0, or at the most 7.5, or at the most 7.0, or at the most 6.9, or at least 6.8, or at least 6.7, or at least 6.6, or at least 6.5, e.g. in the range of 4.5-8.5, or 4.5-8.0, or 4.5-7.5, or 4.5-7.0, such as 4.6-8.0, or 4.6-7.5, or 4.6-7.0, or 4.6-6.9, or 4.7-7.5, or 4.7-7.0, or 4.7-6.7, or 4.8-7.5, or 4.8-7.0, or 4.8-6.6, or 4.9-6.5, or 5.0-6.4.

9. The process according to any one of the preceding paragraphs, wherein the pH of the eluent is at the most 2.1 units higher than the pI of the insulin peptide, e.g. at the most 1.9 units higher, such as at the most 1.7 units higher.

10. The process according to any one of the preceding paragraphs, wherein the pool of the insulin peptide collected in step (b) corresponds to at least 80% by weight, such as at least 85% by weight, or at least 90% by weight, or at least 91% by weight, or at least 92% by weight, or at least 93% by weight, or at least 94% by weight, or at least 95% by weight, or at least 96% by weight, of the insulin peptide applied to the column in step (a).

11. The process according to any one of the preceding paragraphs, wherein the concentration of di- or polyvalent metal ions in the eluent is in the range of 0.1-200 mM, such as 0.5-100 mM, or 1.0-60 mM.

12. The process according to any one of the preceding paragraphs, wherein the ratio between the charge equivalents of di- or polyvalent metal ions in the eluent and the insulin peptide is from 0.1:1 to 50:1, such as from 0.3:1 to 20:1, e.g. from 0.4:1 to 15:1, or from 0.5:1 to 10:1.

13. The process according to any one of the preceding paragraphs, wherein the eluent comprises $Zn^{2+}$ ions, e.g. in concentrations in the range of 0.01-200 mM, such as 0.1-100 mM, e.g. 0.5-75 mM.

14. The process according to any one of the preceding paragraphs, wherein the insulin peptide is selected from insulin peptides, glucagon-like peptides, and exendins, including variants thereof, in particular from insulin peptides including variants thereof.

15. The process according to any one of the preceding paragraphs, wherein the protein-containing solution is obtained from an insulin peptide crystallized with zinc.

16. The process according to any one of the preceding paragraphs, which is a large-scale process wherein the column volume is at least 1 L, or at least 10 L, or at least 20 L, or at least 50 L, or at least 100 L, such as at least 500 L, e.g. at least 1000 L, or at least 5000 L.

17. The process according to any of the preceding paragraphs, wherein the insulin peptide is selected from an insulin derivative which is a naturally occurring insulin or an analogue thereof which has a side chain attached to the α-amino group of the N-terminal amino acid residue of the B chain or to the ε-amino group of a Lys residue present in the B chain of the parent insulin, the side chain being of the general formula:

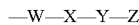

—W—X—Y—Z wherein W is:
  an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
  a chain composed of two, three or four α-amino acid residues linked together via amide bonds, which chain—via an amide bond is—linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the α-amino group of the N-terminal amino acid residue of the B chain or to the ε-amino group of a Lys residue present in the B chain of the parent insulin;

X is:
—CO—;
—CH(COOH)CO—;
—N(CH$_2$COOH)CH$_2$CO—;
—N(CH$_2$COOH)CH$_2$CON(CH$_2$COOH)CH$_2$CO—;
—N(CH$_2$CH$_2$COOH)CH$_2$CH$_2$CO—;
—N(CH$_2$CH$_2$COOH)CH$_2$CH$_2$CON(CH$_2$CH$_2$COOH)CH$_2$CH$_2$CO—;
—NHCH(COOH)(CH$_2$)$_4$NHCO—;
—N(CH$_2$CH$_2$COOH)CH$_2$CO—; or
—N(CH$_2$COOH)CH$_2$CH$_2$CO—.

that a) when W is an amino acid residue or a chain of amino acid residues, via a bond from the underscored carbonyl carbon forms an amide bond with an amino group in W, or b) when W is a covalent bond, via a bond from the underscored carbonyl carbon forms an amide bond with the N-terminal α-amino group in the B chain or with the ε-amino group of a Lys residue present in the B chain of the parent insulin;

Y is:
—(CH$_2$)$_m$— where m is an integer in the range of 6 to 32;

a divalent hydrocarbon chain comprising 1, 2 or 3 —CH=CH— groups and a number of —CH$_2$— groups sufficient to give a total number of carbon atoms in the chain in the range of 10 to 32;

a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H;
and any Zn$^{2+}$ complexes thereof.

18. The process according to any of the preceding paragraphs, wherein the insulin peptide is LysB29(Nε-hexadecandioyl-γ-Glu) des(B30) human insulin.

19. The process according to paragraphs 1-16, wherein the insulin peptide is an insulin derivative having a formula

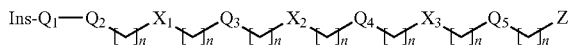

wherein Ins is a parent insulin moiety and Q$_1$-Q$_2$-[CH$_2$]$_n$—X$_1$—[CH$_2$]$_n$-Q$_3$-[CH$_2$]$_n$—X$_2$—[CH$_2$]$_n$-Q$_4$-[CH$_2$]$_n$—X$_3$—[CH$_2$]$_n$-Q$_5$-[CH$_2$]$_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in Q$_1$ or Q$_2$ of the substituent;

each n is independently 0, 1, 2, 3, 4, 5 or 6;
Q$_1$ is:
an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or a bond Q$_2$ is:
—COCH(CONH$_2$)—
—COCH$_2$N(CH$_2$CONH$_2$)—
—COCH$_2$N(CH$_2$CONH$_2$)COCH$_2$N(CH$_2$CONH$_2$)—
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—NH—CO)$_{1-4}$—;
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$; or a bond provided that
at least one of Q$_1$ or Q$_2$ is not a bond, and
that Q$_2$ is not —CO—(CH$_2$)$_2$—CO—NH— when n is 0 or 1, X$_1$ is a bond and Q$_3$ is (CH$_2$CH$_2$O)$_2$—, (CH$_2$CH$_2$O)$_3$— or (CH$_2$CH$_2$OCH$_2$CH$_2$CH$_2$CH$_2$O)— and that if an amine in Q$_1$ or Q$_2$ forms a bond with the rest of the substituent, the amine must be bound to the rest of the substituent via a carbonyl group;

Q$_3$, Q$_4$, and Q$_5$ independently of each other can be
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 4 to 32;
—CO—((CR$^5$R$^6$)$_{1-6}$—NH—CO)—;
—(CO—(CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;
—CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$, where R$^1$ and R$^2$, independently of each other can be H, —CH$_3$ or —(CH)$_{1-6}$—CH$_3$;
(CH$_2$CH$_2$O)$_y$—; (CH$_2$CH$_2$CH$_2$O)$_y$—;
(CH$_2$CH$_2$CH$_2$CH$_2$O)$_y$—;
(CH$_2$CH$_2$OCH$_2$CH$_2$CH$_2$CH$_2$O)$_y$— or
(CH$_2$CH$_2$OCH$_2$CH$_2$CH$_2$CH$_2$O)$_y$—;
—(CH$_2$OCH$_2$)$_y$— where y is 1-20;

arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$, where R$^1$ and R$^2$, independently of each other can be H, —CH$_3$ or —(CH)$_{1-6}$—CH$_3$;

a chain of the formula

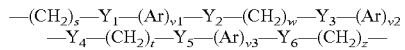

wherein Ar is defined as above, $Y_1$-$Y_6$ independently of each other can be O, S, S=O, SO$_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—(CH$_2$)$_1$—O— does not occur; or a bond;

with the proviso that at least one of $Q_3$-$Q_5$ is not a bond; $X_1$, $X_2$ and $X_3$ are independently of each other

O;

—C=O a bond;

NCOR$^1$, where R$^1$ can be H, —CH$_3$ or —(CH)$_{1-6}$—CH$_3$; or

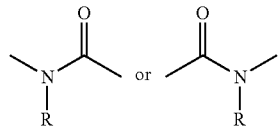

where R is hydrogen, C$_{1-3}$-alkyl, C$_{2-3}$-alkenyl or C$_{2-3}$-alkynyl;

with the proviso that $X_1$, $X_2$ and $X_3$ cannot bind to Z and when $X_1$, $X_2$ and $X_3$ are O, then $X_1$, $X_2$ and $X_3$ do not bind directly to O in $Q_3$, $Q_4$, and $Q_5$ and Z is: —COOH; —CO-Asp; —CO-Glu; —CO-Gly; —CO-Sar; —CH(COOH)$_2$; —N(CH$_2$COOH)$_2$; —SO$_3$H; —OSO$_3$H; —OPO3H$_2$; —PO$_3$H$_2$; -tetrazol-5-yl or —O—W$_1$, where W$_1$ is arylene or heteroarylene, which may be substituted with one or two groups selected from the group consisting of tetrazol-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$, where R$^3$ and R$^4$, independently of each other can be H, —(CH$_2$)$_{1-6}$—SO$_3$H, or —(CH$_2$)$_{1-6}$—O—PO$_3$H$_2$; provided that when Z is —O—W$_1$ then Q$_1$ must be present and any Zn$^{2+}$ complex thereof.

20. A process according to paragraphs 1-16 and 19, wherein the insulin peptide is selected from the group consisting of:

N$^{\epsilon B29}$-ω-carboxy-pentadecanoyl-γ-L-glutamylamide desB30 human insulin, N$^{\epsilon B29}$-ω-carboxy-pentadecanoyl-γ-amino-butanoyl desB30 human insulin, N$^{\epsilon B29}$-ω-carboxy-tetradecanoyl-γ-L-glutamylamide desB30 human insulin, N$^{\epsilon B29}$-ω-carboxy-tridecanoyl-γ-L-glutamylamide desB30 human insulin, N$^{\epsilon B29}$-ω-carboxy-pentadecanoyl-β-alanyl desB30 human insulin, N$^{\epsilon B29}$-ω-carboxy-pentadecanoyl-γ-L-aspartylamide desB30 human insulin, N$^{\epsilon B29}$-ω-carboxy-pentadecanoyl-ε-aminohexanoyl desB30 human insulin, N$^{\epsilon B29}$-ω-carboxy-pentadecanoyl-δ-aminopentanoyl desB30 human insulin, N$^{\epsilon B29}$-10-(4-carboxyphenoxy)-decanoyl-γ-L-glutamylamide desB30 human insulin, N$^{\epsilon B29}$-4-[11-(4-Carboxyphenyl)undecanoylamino]butyryl desB30 human insulin, N$^{\epsilon B29}$-(3-(3-{4-[3-(7-carboxyheptanoylamino)propoxy]butoxy}propylcarbamoyl)-propionyl-γ-glutamylamide) desB30 human Insulin, N$^{\epsilon B29}$-ω-carboxy-tridecanoyl-γ-amino-butanoyl desB30 human insulin, N$^{\epsilon B29}$-ω-carboxy-undecanoyl-γ-amino-butanoyl desB30 human insulin, N$^{\epsilon B29}$-ω-carboxy-tetradecanoyl-γ-amino-butanoyl desB30 human insulin, N$^{\epsilon B29}$-{4-[10-(4-Carboxy-phenoxy)-decanoylamino]-butyryl}desB30 insulin, N$^{\epsilon B29}$-{4-[(14-Carboxy-tetradecanoylamino)-methyl]-benzoyl}desB30 insulin, N$^{\epsilon B29}$-[16-(4-Carboxy-phenoxy)-hexadecanoyl]desB30 insulin, N$^{\epsilon B29}$-{4-[(15-carboxypentadecanoylamino)benzoyl]-desB30 human insulin and N$^{\epsilon B29}$-{4-[(15-Carboxy-pentadecanoylamino)-methyl]-benzoyl}-desB30 insulin 21. A chromatographic process for separating protein components of an insulin-containing solution, said solution comprising an insulin peptide being capable of self-association and/or structural change in the presence of zinc and divalent zinc ions, said process comprising the steps of:

a. applying the insulin-containing solution to a column of an anion exchange chromatographic solid phase material, wherein the loading of the insulin peptide of interest is at least 6.0 g per liter of column volume (g/L$_{CV}$); and b. eluting the insulin peptide of interest from said solid phase material by means of an eluent having a pH of at the most 6.8; and collecting a pool of the insulin peptide of interest corresponding to at least 90% by weight of the insulin peptide of interest applied to the column in step (a).

22. The process according to paragraph 21, wherein the concentration of the zinc ions in the solution is in the range of 0.01-200 mM, such as 0.1-100 mM, e.g. 0.5-75 mM.

23. The process according to any one of the paragraphs 21-22, wherein the ratio between the charge equivalents of the zinc ions and the insulin peptide is typically from 0.1:1 to 50:1, such as from 0.3:1 to 20:1, e.g. from 0.4:1 to 15:1, or from 0.5:1 to 10:1.

24. The process according to any one of paragraphs 21-23, wherein the conductivity of the insulin-containing solution is in the range of 0-100 mS/cm, such as 0-50 mS/cm, e.g. 0-30 mS/cm, or 0.01-100 mS/cm, such as 0.05-50 mS, e.g. 0.1-30 mS/cm.

25. The process according to any one of the preceding paragraphs 21-24, wherein the loading of the insulin peptide is at least 7.0 g/L$_{CV}$, or at least 8.0 g/L$_{CV}$, or at least 8.5 g/L$_{CV}$, or 6.0-50 g/L$_{CV}$, or 7.0-40 g/L$_{CV}$, or 8.0-30 g/L$_{CV}$, such as 8.5-25 g/L$_{CV}$, such as 9.0-20 g/L$_{CV}$, or 9.5-15 g/L$_{CV}$.

26. The process according to any one of preceding paragraphs 21-25, wherein the pH of the eluent is at the most 6.8, such as at the most 6.6, or at the most 6.4, or at the most 6.2, or at the most 6.0, or at least 4.0, or at least 4.4, or at least 4.8, or at least 5.0, e.g. in the range of 4.0-6.8, or 4.4-6.8, or 4.8-6.8, or 4.0-6.6, such as 4.0-6.6, or 4.0-6.4, or 4.0-6.2, or 4.0-6.0, or 4.4-6.8, or 4.4-6.6, or 4.4-6.4, or 4.8-6.8, or 4.8-6.6, or 4.8-6.2, or 5.0-6.8, or 5.0-6.6.

27. The process according to any one of the preceding paragraphs 21-26, wherein the pH of the eluent is at the most 2.1 units higher than the pI of the protein of interest, e.g. at the most 1.9 units higher, such as at the most 1.7 units higher.

28. The process according to any one of the preceding paragraphs 21-27, wherein the pool of the insulin peptide collected in step (b) at least 91% by weight, or at least 92% by weight, or at least 93% by weight, or at least 94% by weight, or at least 95% by weight, or at least 96% by weight, of the insulin peptide applied to the column in step (a).

29. The process according to any one of the preceding paragraphs 21-28, wherein the concentration of zinc ions in the eluent is in the range of 0.1-200 mM, such as 0.5-100 mM, or 1.0-60 mM.

30. The process according to any one of the preceding paragraphs 21-29, wherein the ratio between the charge equivalents of zinc ions in the eluent and the insulin peptide is from 0.1:1 to 50:1, such as from 0.3:1 to 20:1, e.g. from 0.4:1 to 15:1, or from 0.5:1 to 10:1.

31. The process according to any one of the preceding paragraphs 21-30, wherein the eluent comprises $Zn^{2+}$ ions, e.g. in concentrations in the range of 0.01-200 mM, such as 0.1-100 mM, e.g. 0.5-75 mM.

32. The process according to any one of the preceding paragraphs 21-31, which is a large-scale process wherein the column volume is at least 1 L, or at least 10 L, or at least 20 L, or at least 50 L, or at least 100 L, such as at least 500 L, e.g. at least 1000 L, or at least 5000 L.

33. The process according to any one of the preceding paragraphs 21-32, where a washing step is included after step (a) and before the elution step (b) using one, two or several washing buffers.

34. The process according to any one of the preceding paragraphs 21-33, wherein the washing buffer is an aqueous solution comprising a buffering agent comprising at least one component selected from the groups consisting of acids and salts of MES, PIPES, ACES, BES, TES, HEPES, TRIS, histidine, imidazole, glycine, glycylglycine, glycinamide, phosphoric acid, acetic acid (e.g. sodium acetate), lactic acid, glutaric acid, citric acid, tartaric acid, malic acid, maleic acid, and succinic acid.

35. The process according to any one of the preceding paragraphs 21-34, wherein the buffering agent comprises a mixture of two or more components, wherein the mixture is able to provide a pH value in the specified range, e.g by mixture with acetic acid and/or sodium acetate, 36. The process according to any of the preceding paragraphs 21-35, wherein the insulin peptide is selected from an insulin derivative which is a naturally occurring insulin or an analogue thereof which has a side chain attached to the α-amino group of the N-terminal amino acid residue of the B chain or to the ε-amino group of a Lys residue present in the B chain of the parent insulin, the side chain being of the general formula:

—W—X—Y—Z wherein W is:
an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to the α-amino group of the N-terminal amino acid residue of the B chain or to the ε-amino group of a Lys residue present in the B chain of the parent insulin;

X is:
—<u>C</u>O—;
—CH(COOH)<u>C</u>O—;
—N(CH$_2$COOH)CH$_2$<u>C</u>O—;
—N(CH$_2$COOH)CH$_2$CON(CH$_2$COOH)CH$_2$<u>C</u>O—;
—N(CH$_2$CH$_2$COOH)CH$_2$CH$_2$<u>C</u>O—;
—N(CH$_2$CH$_2$COOH)CH$_2$CH$_2$CON(CH$_2$CH$_2$COOH) CH$_2$CH$_2$<u>C</u>O—;
—NHCH(COOH)(CH$_2$)$_4$NH<u>C</u>O—;
—N(CH$_2$CH$_2$COOH)CH$_2$<u>C</u>O—; or
—N(CH$_2$COOH)CH$_2$CH$_2$<u>C</u>O—.

that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

Y is:
(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 10 to 32;
a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H;
and any $Zn^{2+}$ complexes thereof.

37. The process according to any of the preceding paragraphs 21-36, wherein the insulin peptide is LysB29(Nε-hexadecandioyl-γ-Glu) des(B30) human insulin.

38. A chromatographic process according to any of the preceding paragraphs 21-37 for separating protein components of an insulin-containing solution, said solution comprising LysB29(Nε-hexadecandioyl-γ-Glu) des(B30) human insulin and divalent zinc ions, said process comprising the steps of:
a. applying the insulin-containing solution to a column of an anion exchange chromatographic solid phase material, wherein the loading of the insulin peptide of interest is at least 6.0 g per liter of column volume ($g/L_{CV}$); and b. eluting the insulin peptide of interest from said solid phase material by means of an eluent having a pH in the range of 6.4 to 6.8; and collecting a pool of LysB29 (Nε-hexadecandioyl-γ-Glu) des(B30) human insulin corresponding to at least 90% by weight of LysB29 (Nε-hexadecandioyl-γ-Glu) des(B30) human insulin applied to the column in step (a).

39. The process according to paragraph 1 and 38, wherein a washing step is included after step (a) and before the elution step (b) using a washing buffer comprising ethanol and treethanolamine.

40. The process according to paragraphs 21-35, wherein the insulin peptide is an insulin derivative having a formula

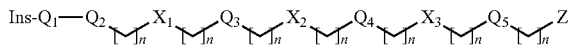

wherein Ins is a parent insulin moiety and $Q_1$-$Q_2$-$[CH_2]_n$—$X_1$—$[CH_2]_n$-$Q_3$-$[CH_2]_n$—$X_2$—$[CH_2]_n$-$Q_4$-$[CH_2]_n$—$X_3$—$[CH_2]_n$-$Q_5$-$[CH_2]_n$—$Z$ is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

each n is independently 0, 1, 2, 3, 4, 5 or 6;

$Q_1$ is:

an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or a bond $Q_2$ is:

—COCH(CONH$_2$)—

—COCH$_2$N(CH$_2$CONH$_2$)—

—COCH$_2$N(CH$_2$CONH$_2$)COCH$_2$N(CH$_2$CONH$_2$)—

—COCH$_2$CH$_2$N(CH$_2$CH$_2$CONH$_2$)—

—COCH$_2$CH$_2$N(CH$_2$CH$_2$CONH$_2$)—COCH$_2$CH$_2$N(CH$_2$CH$_2$CONH$_2$)—

—COCH$_2$N(CH$_2$CH$_2$CONH$_2$)—

—COCH$_2$CH$_2$N(CH$_2$CONH$_2$)—

—COCH$_2$OCH$_2$CONH—

—CO—((CR$^5$R$^6$)$_{1-6}$—NH—CO)$_{1-4}$—;

—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$; or a bond provided that at least one of $Q_1$ or $Q_2$ is not a bond, and that $Q_2$ is not —CO—(CH$_2$)$_2$—CO—NH— when n is 0 or 1, $X_1$ is a bond and $Q_3$ is (CH$_2$CH$_2$O)$_2$—, (CH$_2$CH$_2$O)$_3$— or (CH$_2$CH$_2$OCH$_2$CH$_2$CH$_2$CH$_2$O)— and that if an amine in $Q_1$ or $Q_2$ forms a bond with the rest of the substituent, the amine must be bound to the rest of the substituent via a carbonyl group;

$Q_3$, $Q_4$, and $Q_5$ independently of each other can be

—(CH$_2$)$_m$— where m is an integer in the range of 6 to 32;

a divalent hydrocarbon chain comprising 1, 2 or 3 —CH=CH— groups and a number of —CH$_2$— groups sufficient to give a total number of carbon atoms in the chain in the range of 4 to 32;

—CO—((CR$^5$R$^6$)$_{1-6}$—NH—CO)—;

—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$;

—CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$, where R$^1$ and R$^2$, independently of each other can be H, —CH$_3$ or —(CH)$_{1-6}$—CH$_3$;

(CH$_2$CH$_2$O)$_y$—; (CH$_2$CH$_2$CH$_2$O)$_y$—; (CH$_2$CH$_2$CH$_2$CH$_2$O)$_y$—;

(CH$_2$CH$_2$OCH$_2$CH$_2$CH$_2$CH$_2$O)$_y$— or (CH$_2$CH$_2$CH$_2$OCH$_2$CH$_2$CH$_2$CH$_2$O)$_y$—;

—(CH$_2$OCH$_2$)$_y$— where y is 1-20;

arylene or heteroarylene, which may be substituted with one or two groups selected from the group consisting of —CH$_3$, —(CH)$_{1-6}$—CH$_3$, —CONR$^1$R$^2$ or —SO$_2$NR$^1$R$^2$, where R$^1$ and R$^2$, independently of each other can be H, —CH$_3$ or —(CH)$_{1-6}$—CH$_3$;

a chain of the formula

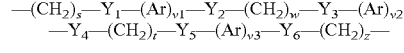

wherein Ar is defined as above, $Y_1$-$Y_6$ independently of each other can be O, S, S=O, SO$_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—(CH$_2$)$_1$—O— does not occur; or a bond;

with the proviso that at least one of $Q_3$-$Q_5$ is not a bond;

$X_1$, $X_2$ and $X_3$ are independently of each other

O;

—C=O a bond;

NCOR$^1$, where R$^1$ can be H, —CH$_3$ or —(CH)$_{1-6}$—CH$_3$; or

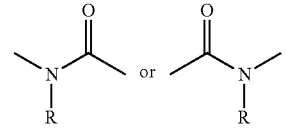

where R is hydrogen, C$_{1-3}$-alkyl, C$_{2-3}$-alkenyl or C$_{2-3}$-alkynyl;

with the proviso that $X_1$, $X_2$ and $X_3$ cannot bind to Z and when $X_1$, $X_2$ and $X_3$ are O, then $X_1$, $X_2$ and $X_3$ do not bind directly to O in $Q_3$, $Q_4$, and $Q_5$ and Z is: —COOH; —CO-Asp; —CO-Glu; —CO-Gly; —CO-Sar; —CH(COOH)$_2$; —N(CH$_2$COOH)$_2$; —SO$_3$H; —OSO$_3$H; —OPO3H$_2$; —PO$_3$H$_2$; -tetrazol-5-yl or —O—W$_1$, where W$_1$ is arylene or heteroarylene, which may be substituted with one or two groups selected from the group consisting of tetrazol-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$, where R$^3$ and R$^4$, independently of each other can be H, —(CH$_2$)$_{1-6}$—SO$_3$H, or —(CH$_2$)$_{1-6}$—O—PO$_3$H$_2$; provided that when Z is —O—W$_1$ then Q$_1$ must be present and any Zn$^{2+}$ complex thereof.

41. A process according to paragraphs 21-35 and 40, wherein the insulin peptide is selected from the group consisting of: N$^{\epsilon B29}$-ω-carboxy-pentadecanoyl-γ-L-glutamylamide desB30 human insulin, N$^{\epsilon B29}$-ω-carboxy-pentadecanoyl-γ-amino-butanoyl desB30 human insulin, N$^{\epsilon B29}$-ω-carboxy-tetradecanoyl-γ-L-glutamylamide desB30 human insulin, N$^{\epsilon B29}$-ω-carboxy-tridecanoyl-γ-L-glutamylamide desB30 human insulin, N$^{\epsilon B29}$-ω-carboxy-pentadecanoyl-β-alanyl desB30 human insulin, N$^{\epsilon B29}$-ω-carboxy-pentadecanoyl-γ-L-aspartylamide desB30 human insulin, N$^{\epsilon B29}$-ω-carboxy-pentadecanoyl-ε-aminohexanoyl desB30 human insulin, N$^{\epsilon B29}$-ω-carboxy-pentadecanoyl-δ-aminopentanoyl desB30 human insulin, N$^{\epsilon B29}$-10-(4-carboxyphenoxy)-decanoyl-γ-L-glutamylamide desB30 human insulin, N$^{\epsilon B29}$-4-[11-(4-Carboxyphenyl) undecanoylamino]butyryl desB30 human insulin, N$^{\epsilon B29}$-(3-(3-{4-[3-(7-carboxyheptanoylamino)propoxy]butoxy}propylcarbamoyl)-propionyl-γ-glutamylamide) desB30 human Insulin, N$^{\epsilon B29}$-ω-carboxy-tridecanoyl-γ-amino-butanoyl desB30 human insulin, N$^{\epsilon B29}$-ω-carboxy-undecanoyl-γ-amino-butanoyl desB30 human insulin, N$^{\epsilon B29}$-ω-carboxy-tetradecanoyl-γ-amino-butanoyl desB30 human insulin, N$^{\epsilon B29}$-{4-[10-(4-Carboxy-phenoxy)-decanoylamino]-butyryl}desB30 insulin, N$^{\epsilon B29}$-{4-[(14-Carboxy-tetradecanoylamino)-methyl]-benzoyl}desB30 insulin, N$^{\epsilon B29}$-[16-(4-Carboxy-phenoxy)-hexadecanoyl]desB30 insulin, N$^{\epsilon B29}$-{4-[(15-carboxypentadecanoylamino)benzoyl]-desB30 human insulin and N$^{\epsilon B29}$-{4-[(15-Carboxy-pentadecanoylamino)-methyl]-benzoyl}-desB30 insulin 42. A method of controlling peak shape in ion-exchange chromatography of insulin peptides being capable of self-association and/or structural change in the presence of di- or polyvalent metal ions by using a. di- or polyvalent metal ions to obtain optimal separation of the insulin peptide and related impurities wherein divalent metal ions have been added to secure a fronting peak shape of the insulin peptide, where the related impurities elutes before the insulin peptide.

43. A method according to paragraph 42, wherein the di- or polyvalent metal ions are selected from Zn$^{2+}$, Ca$^{2+}$, Mg$^{2+}$, Ni$^{2+}$, Cu$^{2+}$, Ba$^{2+}$, preferably Zn$^{2+}$.

44. The method according to paragraphs 42-43, wherein the insulin peptides are eluted with and eluent having a pH at the most 6.8, such as at the most 6.6, or at the most 6.4, or at the most 6.2, or at the most 6.0, or at least 4.0, or at least 4.4, or at least 4.8, or at least 5.0, e.g. in the range of 4.0-6.8, or 4.4-6.8, or 4.8-6.8, or 4.0-6.8, such as 4.0-6.6, or 4.0-6.4, or 4.0-6.2, or 4.0-6.0, or 4.4-6.8, or 4.4-6.6, or 4.4-6.4, or 4.8-6.8, or 4.8-6.6, or 4.8-6.2, or 5.0-6.8, or 5.0-6.6.

45. The method according to any one of the preceding paragraphs 42-44, wherein the number of di- or polyvalent metal ions is more than 4 metal ions per 6 molecules insulin peptide.

46. The method according to any one of the preceding paragraphs 42-45, wherein the number of di- or polyvalent metal ions is more than 4.5 metal ions per 6 molecules insulin peptide.

47. The method according to any one of the preceding paragraphs 42-46, wherein the number of di- or polyvalent metal ions is more than 5 metal ions per 6 molecules insulin peptide, more than 5.5 metal ions per 6 molecules insulin peptide, more than 6 metal ions per 6 molecules insulin peptide or more than 6.5 metal ions per 6 molecules insulin peptide.

48. The method according to any one of the preceding paragraphs 42-47, wherein the number of di- or polyvalent metal ions is up to 12 metal ions per 6 molecules insulin peptide, 49. The method according to any one of the preceding paragraphs 42-48, wherein the ratio between the charge equivalents of the di- or polyvalent metal ions and the insulin peptide is typically from 0.1:1 to 50:1, such as from 0.3:1 to 20:1, e.g. from 0.4:1 to 15:1, or from 0.5:1 to 10:1.

50. The method according to any one of the preceding paragraphs 42-49, wherein the conductivity of the insulin-containing solution is in the range of 0-100 mS/cm, such as 0-50 mS/cm, e.g. 0-30 mS/cm, or 0.01-100 mS/cm, such as 0.05-50 mS, e.g. 0.1-30 mS/cm.

51. The method according to any one of the preceding paragraphs 42-50, wherein the pH of the eluent is at the most 2.1 units higher than the pI of the protein of interest, e.g. at the most 1.9 units higher, such as at the most 1.7 units higher.

52. The method according to any one of the preceding paragraphs 42-51, wherein the fronting peak shape is controlled so that at least 90% by weight, or at least 91% by weight, or at least 92% by weight, or at least 93% by weight, or at least 94% by weight, or at least 95% by weight, or at least 96% by weight, of the insulin peptide is separated from the related impurities.

53. The method according to any one of the preceding paragraphs 42-52, wherein the concentration of di- or polyvalent metal ions in the eluent is in the range of 0.1-200 mM, such as 0.5-100 mM, or 1.0-60 mM.

54. The method according to any one of the preceding paragraphs 42-53, wherein the ratio between the charge equivalents of di- or polyvalent metal ions in the eluent and the protein of interest is from 0.1:1 to 50:1, such as from 0.3:1 to 20:1, e.g. from 0.4:1 to 15:1, or from 0.5:1 to 10:1.

55. The method according to any one of the preceding paragraphs 42-54, wherein the eluent comprises Zn$^{2+}$ ions, e.g. in concentrations in the range of 0.01-200 mM, such as 0.1-100 mM, e.g. 0.5-75 mM.

56. The method according to any one of the preceding paragraphs 42-55, wherein the insulin peptide is self-associated with zinc ions.

57. The method according to any one of the preceding paragraphs 42-56, wherein the insulin peptide is selected from an insulin derivative which is a naturally occurring insulin or an analogue thereof which has a side chain attached to the α-amino group of the N-terminal amino acid residue of the B chain or to the ε-amino group of a Lys residue present in the B chain of the parent insulin, the side chain being of the general formula:

wherein W is:
an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to the α-amino group of the N-terminal amino acid residue of the B chain or to the ε-amino group of a Lys residue present in the B chain of the parent insulin;
—$\underline{C}$O—;
—CH(COOH)$\underline{C}$O—;
—N(CH$_2$COOH)CH$_2$$\underline{C}$O—;
—N(CH$_2$COOH)CH$_2$CON(CH$_2$COOH)CH$_2$$\underline{C}$O—;
—N(CH$_2$CH$_2$COOH)CH$_2$CH$_2$$\underline{C}$O—;
—N(CH$_2$CH$_2$COOH)CH$_2$CH$_2$CON(CH$_2$CH$_2$COOH)CH$_2$CH$_2$$\underline{C}$O—;
—NHCH($\overline{C}$OOH)(CH$_2$)$_4$NH$\underline{C}$O—;
—N(CH$_2$CH$_2$COOH)CH$_2$$\underline{C}$O—; or
—N(CH$_2$COOH)CH$_2$CH$_2$$\underline{C}$O—.
that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;
Y is:
—(CH$_2$)$_m$— where m is an integer in the range of 6 to 32;
a divalent hydrocarbon chain comprising 1, 2 or 3 —CH═CH— groups and a number of —CH$_2$— groups sufficient to give a total number of carbon atoms in the chain in the range of 10 to 32;
a divalent hydrocarbon chain of the formula —(CH$_2$)$_v$C$_6$H$_4$(CH$_2$)$_w$— wherein v and w are integers or one of them is zero so that the sum of v and w is in the range of 6 to 30; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H;
and any Zn$^{2+}$ complexes thereof.

58. The process according to any of the preceding paragraphs 42-57, wherein the insulin peptide is LysB29(N$^\epsilon$-hexadecandioyl-γ-Glu) des(B30) human insulin.

59. The process according to paragraphs 42-56, wherein the insulin peptide is an insulin derivative having a formula:

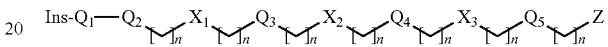

wherein Ins is a parent insulin moiety and Q$_1$-Q$_2$-[CH$_2$]$_n$—X$_1$—[CH$_2$]$_n$-Q$_3$-[CH$_2$]$_n$—X$_2$—[CH$_2$]$_n$-Q$_4$-[CH$_2$]$_n$—X$_3$—[CH$_2$]$_n$-Q$_5$-[CH$_2$]$_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in Q$_1$ or Q$_2$ of the substituent;
each n is independently 0, 1, 2, 3, 4, 5 or 6;
Q$_1$ is:
an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or
a chain composed of two, three or four α-amino acid amide or amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or
a bond
Q$_2$ is:
—COCH(CONH$_2$)—
—COCH$_2$N(CH$_2$CONH$_2$)—
—COCH$_2$N(CH$_2$CONH$_2$)COCH$_2$N(CH$_2$CONH$_2$)
—COCH$_2$CH$_2$N(CH$_2$CH$_2$CONH$_2$)—
—COCH$_2$CH$_2$N(CH$_2$CH$_2$CONH$_2$)—COCH$_2$CH$_2$N(CH$_2$CH$_2$CONH$_2$)—
—COCH$_2$N(CH$_2$CH$_2$CONH$_2$)—
—COCH$_2$CH$_2$N(CH$_2$CONH$_2$)—
—COCH$_2$OCH$_2$CONH—
—CO—((CR$^5$R$^6$)$_{1-6}$—NH—CO)$_{1-4}$—;
—CO—((CR$^5$R$^6$)$_{1-6}$—CO—NH)$_{1-4}$—, where R$^5$ independently can be H, —CH$_3$, —(CH$_2$)$_{1-6}$CH$_3$ or —CONH$_2$ and R$^6$ independently can be H, —CH$_3$, —(CH$_2$)$_{1-6}$CH$_3$; or
a bond
provided that
at least one of Q$_1$ or Q$_2$ is not a bond, and that Q$_2$ is not —CO—(CH$_2$)$_2$—CO—NH— when n is 0 or 1, X$_1$ is a bond and $Q_3$ is $(CH_2CH_2O)_2—$, $(CH_2CH_2O)_3—$ or $(CH_2CH_2OCH_2CH_2CH_2CH_2O)—$ and that if an amine in $Q_1$ or $Q_2$ forms a bond with the rest of the substituent, the amine must be bound to the rest of the substituent via a carbonyl group;

$Q_3$, $Q_4$, and $Q_5$ independently of each other can be

—$(CH_2)_m$— where m is an integer in the range of 6 to 32;

a divalent hydrocarbon chain comprising 1, 2 or 3 —CH=CH— groups and a number of —$CH_2$— groups sufficient to give a total number of carbon atoms in the chain in the range of 4 to 32;

—CO—$((CR^5R^6)_{1-6}$—NH—CO)—;

—(CO—$(CR^5R^6)_{1-6}$—CO—NH$)_{1-4}$—, where $R^5$ independently can be H, —$CH_3$, —$(CH_2)_{1-6}CH_3$ or $CONH_2$ and $R^6$ independently can be H, —$CH_3$, —$(CH_2)_{1-6}CH_3$;

—CO—$(CH_2)_{0-3}$—Ar—$(CH_2)_{0-3}$— where Ar can be arylene or heteroarylene, which may be substituted with one or two groups selected from the group consisting of —$CH_3$, —$(CH)_{1-6}$—$CH_3$, —$CONR^1R^2$ or —$SO_2NR^1R^2$, where $R^1$ and $R^2$, independently of each other can be H, —$CH_3$ or —$(CH)_{1-6}$—$CH_3$;

$(CH_2CH_2O)_y$—; $(CH_2CH_2CH_2O)_y$—; $(CH_2CH_2CH_2CH_2O)_y$—; $(CH_2CH_2OCH_2CH_2CH_2CH_2O)_y$— or $(CH_2CH_2CH_2OCH_2CH_2CH_2CH_2O)_y$—; —$(CH_2OCH_2)_y$— where y is 1-20;

arylene or heteroarylene, which may be substituted with one or two groups selected from the group consisting of —$CH_3$, —$(CH)_{1-6}$—$CH_3$, —$CONR^1R^2$ or —$SO_2NR^1R^2$, where $R^1$ and $R^2$, independently of each other can be H, —$CH_3$ or —$(CH)_{1-6}$—$CH_3$;

a chain of the formula

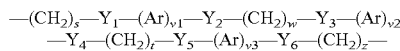

wherein Ar is defined as above, $Y_1$-$Y_6$ independently of each other can be O, S, S=O, $SO_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—$(CH_2)_1$—O— does not occur; or a bond;

with the proviso that at least one of $Q_3$-$Q_5$ is not a bond;

$X_1$, $X_2$ and $X_3$ are independently of each other

O;

—C=O a bond;

$NCOR^1$, where $R^1$ can be H, —$CH_3$ or —$(CH)_{1-6}$—$CH_3$; or

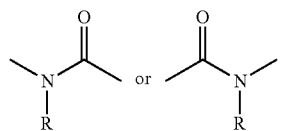

where R is hydrogen, $C_{1-3}$-alkyl, $C_{2-3}$-alkenyl or $C_{2-3}$-alkynyl;

with the proviso that $X_1$, $X_2$ and $X_3$ cannot bind to Z and when $X_1$, $X_2$ and $X_3$ are O, then $X_1$, $X_2$ and $X_3$ do not bind directly to O in $Q_3$, $Q_4$, and $Q_5$ and Z is: —COOH; —CO-Asp; —CO-Glu; —CO-Gly; —CO-Sar; —CH(COOH)$_2$; —N(CH$_2$COOH)$_2$; —SO$_3$H; —OSO$_3$H; —OPO3H$_2$; —PO$_3$H$_2$; -tetrazol-5-yl or —O—$W_1$, where $W_1$ is arylene or heteroarylene, which may be substituted with one or two groups selected from the group consisting of tetrazol-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$, where R$^3$ and R$^4$, independently of each other can be H, —(CH$_2$)$_{1-6}$—SO$_3$H, or —(CH$_2$)$_{1-6}$—O—PO$_3$H$_2$;

provided that when Z is —O—$W_1$ then $Q_1$ must be present and any $Zn^{2+}$ complex thereof.

60. A process according to paragraphs 42-56 and 59, wherein the insulin peptide is selected from the group consisting of:

$N^{\epsilon B29}$-ω-carboxy-pentadecanoyl-γ-L-glutamylamide desB30 human insulin, $N^{\epsilon B29}$-ω-carboxy-pentadecanoyl-γ-amino-butanoyl desB30 human insulin, $N^{\epsilon B29}$-ω-carboxy-tetradecanoyl-γ-L-glutamylamide desB30 human insulin, $N^{\epsilon B29}$-ω-carboxy-tridecanoyl-γ-L-glutamylamide desB30 human insulin, $N^{\epsilon B29}$-ω-carboxy-pentadecanoyl-β-alanyl desB30 human insulin, $N^{\epsilon B29}$-ω-carboxy-pentadecanoyl-γ-L-aspartylamide desB30 human insulin, $N^{\epsilon B29}$-ω-carboxy-pentadecanoyl-ε-aminohexanoyl desB30 human insulin, $N^{\epsilon B29}$-ω-carboxy-pentadecanoyl-δ-aminopentanoyl desB30 human insulin, $N^{\epsilon B29}$-10-(4-carboxyphenoxy)-decanoyl-γ-L-glutamylamide desB30 human insulin, $N^{\epsilon B29}$-4-[11-(4-Carboxyphenyl)undecanoylamino]butyryl desB30 human insulin, $N^{\epsilon B29}$-(3-(3-{4-[3-(7-carboxyheptanoylamino)propoxy]butoxy}propylcarbamoyl)-propionyl-γ-glutamylamide) desB30 human Insulin, $N^{\epsilon B29}$-ω-carboxy-tridecanoyl-γ-amino-butanoyl desB30 human insulin, $N^{\epsilon B29}$-ω-carboxy-undecanoyl-γ-amino-butanoyl desB30 human insulin, $N^{\epsilon B29}$-ω-carboxy-tetradecanoyl-γ-amino-butanoyl desB30 human insulin, $N^{\epsilon B29}$-{4-[10-(4-Carboxy-phenoxy)-decanoylamino]-butyryl}desB30 insulin, $N^{\epsilon B29}$-{4-[(14-Carboxy-tetradecanoylamino)-methyl]-benzoyl}desB30 insulin, $N^{\epsilon B29}$-[16-(4-Carboxy-phenoxy)-hexadecanoyl]desB30 insulin, $N^{\epsilon B29}$-{4-[(15-carboxypentadecanoylamino)benzoyl]-desB30 human insulin and $N^{\epsilon B29}$-{4-[(15-Carboxy-pentadecanoylamino)-methyl]-benzoyl}-desB30 insulin 61. Purified insulin peptide produced by the process or method of any of the preceding paragraphs.

EXAMPLE 1

A column with the dimensions d=1 cm and L=25 cm is packed with Source 30Q from GE Healthcare.

A protein-containing solution containing 12 g/L insulin peptide (LysB29(Nε-hexadecandioyl-γ-Glu) des(B30) human insulin) (pI=4.7) in 30% EtOH, at pH=7.5 with a conductivity <3 mS/cm is applied to the column at a load of 8, 10, and 12 g/$L_{CV}$. The protein-containing solution contains Zn-ions in an amount of 2 zinc atoms per six insulin molecules.

Two buffer containing 42.5% ethanol, and 20 mM triethanolamine at pH=6.4, 6.8 and 7.2, containing 0 mM and 300 mM $NH_4Ac$ (Ammonium acetate) are used for elution. After the application of the protein-containing solution, the column is washed using one column volume of the solvent containing 0 mM $NH_4Ac$ and hereafter the protein is eluted using a salt gradient from 30 mM to 180 mM $NH_4Ac$ over 15 column volumes (see FIG. 1). Yields for all experiments were above 90%.

The result is shown in FIGS. 1-3 and further explained below.

FIG. 1: At pH 6.4 the impurity eluting before the main peak (at V–$V_{Reg}$≈80 mL) is clearly separated from the main peak both at a low and a high load (8 and 12 g/L). The collected pool volume from app. −70 and −60 mL to 0 mL is small and the product concentration in the pool is high.

FIG. 2: At pH 6.8 the impurity eluting before the main peak (at V–$V_{Reg}$≈80 mL) is separated from the main peak at a load of 10 g/L. The collected pool volume from app. −80 is larger and the product concentration is smaller than at pH 6.4.

FIG. 3: At pH 7.2 the impurity eluting is eluting before the main peak (at V–$V_{Reg}$≈85 mL) at a low load, 8 g/L, but without baseline separation as seen at pH 6.4 at a low load. When the load is increased to 12 g/L the impurity is no longer separated from the product but is displaced of the product (at V–$V_{Reg}$≈120 mL). The pool volume is large and the and concentration is the pool is hence lower than seen at lower pH-values

EXAMPLE 2

An experiment was made where samples were taken out to analyse the content of $Zn^{2+}$ in each of the fractions (see FIG. 4). These samples show that Zn is eluting together with the

| Sample | Content of Zn in collected fractions $Zn^{2+}$ [mg/L] |
|---|---|
| 1. Fraction collected before related impurity (fraction no. 12-23) | 0.2 |
| 2. Fraction collected at related impurity eluting before main peak (fraction no. 45-47) | 1.2 |
| 3. Pool | 6 |
| 4. Fraction collected after the pool (fraction no. 1-4) | 0.54 |

The numbers of the fractions in above table corresponds to the fractions shown in FIG. 4.

It is clearly seen that the $Zn^{2+}$ is eluting together with the product.

The samples taken from a chromatographic run (sample 1-4) where $Zn^{2+}$ was present in the feed but not in the eluents shows that $Zn^{2+}$ is present in much higher concentration in the pool containing the product, where the concentration of the insulin analogue is the highest, compared to samples taken around the pool. This shows the strong interaction/cooperativity between insulin and $Zn^{2+}$.

Comparing the chromatogram in FIG. 4 with a traditional Langmurian chromatogram it is seen that the rear part of the chromatogram is concave downward, whereas a traditional Langmurian chromatogram is concave upward. This indicates that also at these pH-values the peak shape is influenced by the $Zn^{2+}$.

The presence of a di- or polyvalent metallic ion in the protein-containing solution in combination with adjustment of the pH in the eluent to balance attractive and repulsive forces and hereby create an isotherm which is linear to higher concentrations lead to a small pool volume and a high pool concentration.

The co-operativity can be seen in the chromatogram where the main peak will be fronting, and move away from the impurity eluting before the main peak.

Insulin peak profiles changing from a tailing peak at high pH (thin dotted curve in FIG. 3, pH=7.2), similar to the behaviour of a Langmurian profile of somewhat tailing at set point pH (solid thin curve in FIG. 2, pH=6.8), to fronting peak profile at low pH (thick dashed curve in FIG. 1, pH=6.4), by the presence of $Zn^{2+}$ in the mobile phase, i.e. the protein-containing solution (FIG. 1-3). The high and low pH experiments have been conducted at a high and a low load, which can be seen from the area below the curves, whereas the experiments at pH=6.8 have been run at a load between the load of the other experiments. All experiments have been repeated to confirm the findings and all chromatograms are aligned to the end of the pool collection to make them easier to compare. The critical impurity to be removed is eluting before the main peak e.g. at pH=6.8 this is eluting around −90 mL. It is seen that at this pH and the high pH the peaks are clearly tailing (steep front and flat tail). At the high pH the separation between the product and the impurity is seen to be very poor, especially at high load, where no clear peak is seen eluting before the main peak. At the low pH the peaks are fronting (flat front and steep tail), and a baseline separation is seen between the impurity and the product peak. This fronting has a number of advantages in this case: (a) The product peak is moving away from the impurity; (b) The pool concentration is higher, which can be seen from the higher UV-signal; and (c) It is possible to increase the load on the column, still removing the impurity.

EXAMPLE 3

Analysis of Self-Association of Insulin by the SEC Method

The ability of insulin peptides to self-associate can be analysed by the SEC method. Analysis by size exclusion chromatography (SEC) on a Superose 6 PC column (0.32*30 cm) using isotonic 10 mM tris-buffered saline optionally added 2 mM phenol at 37° C. and pH 7.3, injection volume of 20 μL, flow of 0.05 mL/min and run time 130 min. First reference of Blue dextran (>>5 MDa, $K_{AV}$ 0.0), Thyroglobulin (669 kDa, $K_{AV}$ 0.28), Ferritin (440 kDa, $K_{AV}$ 0.39), Ovalbumin (44.5 kDa, $K_{AV}$ 0.56), Ribonuclease (13.7 kDa, $K_{AV}$ 0.69) and a second reference of Albumin (66 kDa, $K_{AV}$ 0.53), Co(III)insulin-hexamer (35 kDa, $K_{AV}$ 0.61), and monomeric insulin X2 (6 kDa, $K_{AV}$ 0.73). Retention time of blue dextran was 17.9 min ($t_0$) and 0.74 min without column ($t_d$), and retention time of albumin (HSA) was about 34.1 min, $K_{AV}=(t-t_0)/(V/f+t_d-t_0)$ with t: retention time (min)
$t_0$: retention time of blue dextran (exclusion limit)
$t_d$: retention time of blue dextran without column (void volume)
$V_t$: total column volume (mL)
f: flow (mL/min)

Data Format:

| | |
|---|---|
| $K_{AV}$ peak1 | x.xx |
| Area peak1 (%) | xxx |
| $K_{AV}$ peak2 | x.xx |
| Area peak2 (%) | xxx |

$K_{AV}$ area peak1 is measured from $K_{AV}=0$ to $K_{AV}=0.46$ (32 min) as relative area % of total area for $K_{AV}<0.46$ corresponding to self association larger than albumin. For $K_{AV}$ peak 1 about 0.56 (albumin size) integration cut is between albumin size and insulin hexamer size.

EXAMPLE 4

Analysis of Insulin Receptor Binding

The affinity of the insulin peptide for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 µl of a 1:5000 diluted purified recombinant human insulin receptor—exon 11, an amount of a stock solution of A14 Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl was then added and a dilution series is made from appropriate samples. To the dilution series was then added 100 µl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

The invention claimed is:

1. A chromatographic process for separating protein components said process comprising the steps of:
   a. applying a protein-containing solution to a column of a chromatographic solid phase material, wherein the protein-containing solution comprises an insulin peptide and one or more di- or polyvalent metal ions, wherein the loading of the insulin peptide is at least 6.0 g per liter of column volume (g/$L_{CV}$); and
   b. eluting the insulin peptide from said solid phase material by means of an eluent having a pH of at the most 8.5; and collecting a pool of the insulin peptide corresponding to at least 75% by weight of the insulin peptide applied to the column in step (a);
and
wherein the insulin peptide is capable of self-association and/or structural change in the presence of the di- or polyvalent metal ions.

2. A chromatographic process for separating protein components of an insulin-containing solution, said solution comprising an insulin peptide being capable of self-association and/or structural change in the presence of zinc and divalent zinc ions, said process comprising the steps of:
   a. applying the insulin-containing solution to a column of an anion exchange chromatographic solid phase material, wherein the loading of the insulin peptide of interest is at least 6.0 g per liter of column volume (g/$L_{CV}$); and
   b. eluting the insulin peptide of interest from said solid phase material by means of an eluent having a pH of at the most 6.8; and collecting a pool of the insulin peptide of interest corresponding to at least 90% by weight of the insulin peptide of interest applied to the column in step (a).

3. The process of claim 1, wherein the divalent metal ion is zinc' and the concentration of the zinc ions in the solution is in the range of 0.01-200 mM.

4. The process of claim 3, wherein the ratio between the charge equivalents of the zinc ions and the insulin peptide is from 0.1:1 to 50:1.

5. The process of claim 1, wherein the pH of the eluent is at the most 6.8.

6. The process of claim 1, wherein the pool of the insulin peptide collected in step (b) is at least 91% by weight of the insulin peptide applied to the column in step (a).

7. The process of claim 1, wherein the insulin peptide is an insulin derivative, which has a side chain attached to the α-amino group of the N-terminal amino acid residue of the B chain or to the ε-amino group of a Lys residue present in the B chain of the parent insulin, the side chain being of the general formula:

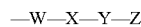
—W—X—Y—Z wherein W is:
   an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
   a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the α-amino acid residues of W being selected from the group of α-amino acid residues having a neutral side chain and α-amino acid residues having a carboxylic acid group in the side chain so that W has at least one α-amino acid residue which has a carboxylic acid group in the side chain; or
   a covalent bond from X to the α-amino group of the N-terminal amino acid residue of the B chain or to the ε-amino group of a Lys residue present in the B chain of the parent insulin;

X is:
   —CO—;
   —CH(COOH)CO—;
   —N(CH$_2$COOH)CH$_2$CO—;
   —N(CH$_2$COOH)CH$_2$CON(CH$_2$COOH)CH$_2$CO—;
   —N(CH$_2$CH$_2$COOH)CH$_2$CH$_2$CO—;
   —N(CH$_2$CH$_2$COOH)CH$_2$CH$_2$CON(CH$_2$CH$_2$COOH)CH$_2$CH$_2$CO—;
   —NHCH(COOH)(CH$_2$)$_4$NHCO—;
   —N(CH$_2$CH$_2$COOH)CH$_2$CO—; or
   —N(CH$_2$COOH)CH$_2$CH$_2$CO—;
that
a) when W is an α-amino acid residue or a chain of α-amino acid residues, via a bond from the underscored carbonyl carbon forms an amide bond with an amino group in W, or b) when W is a covalent bond, via a bond from the underscored carbonyl carbon forms an amide bond with the N-terminal α-amino group in the B chain or with the ε-amino group of a Lys residue present in the B chain of the parent insulin;

Y is:
—$(CH_2)_m$— where m is an integer in the range of 6 to 32;
a divalent hydrocarbon chain comprising 1, 2 or 3 —CH═CH— groups and a number of —$CH_2$— groups sufficient to give a total number of carbon atoms in the chain in the range of 10 to 32;
a divalent hydrocarbon chain of the formula —$(CH_2)_vC_6H_4(CH_2)_w$— wherein v and w are integers or one of them is zero so that the sum of v and w is in the range of 6 to 30; and Z is:
—COOH;
—CO-Asp;
—CO-Glu;
—CO-Gly;
—CO-Sar;
—$CH(COOH)_2$;
—$N(CH_2COOH)_2$;
—$SO_3H$; or
—$PO_3H$;
and any $Zn^{2+}$ complexes thereof.

8. The process of claim 7, wherein the insulin peptide is LysB29(Nε-hexadecandioyl-γ-Glu) des(B30) human insulin.

9. The process of claim 1 for separating protein components of an insulin-containing solution, said solution comprising LysB29(Nε-hexadecandioyl-γ-Glu) des(B30) human insulin and divalent zinc ions, said process comprising the steps of:
   a. applying the insulin-containing solution to a column of an anion exchange chromatographic solid phase material, wherein the loading of the insulin peptide of interest is at least 6.0 g per liter of column volume ($g/L_{CV}$); and
   b. eluting the insulin peptide of interest from said solid phase material by means of an eluent having a pH in the range of 6.4 to 6.8; and collecting a pool of LysB29(Nε-hexadecandioyl-γ-Glu) des(B30) human insulin corresponding to at least 90% by weight of LysB29(Nε-hexadecandioyl-γ-Glu) des(B30) human insulin applied to the column in step (a).

10. The process of claim 1, wherein a washing step is included after step (a) and before the elution step (b) using a washing buffer comprising ethanol and triethanolamine.

11. The process of claim 1, wherein the insulin peptide is an insulin derivative having a formula:

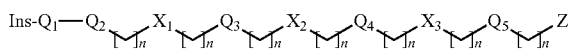

wherein Ins is a parent insulin moiety and $Q_1$-$Q_2$-$[CH_2]_n$—$X_1$—$[CH_2]_n$-$Q_3$-$[CH_2]_n$—$X_2$—$[CH_2]_n$-$Q_4$-$[CH_2]_n$—$X_3$—$[CH_2]_n$-$Q_5$-$[CH_2]_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

each n is independently 0, 1, 2, 3, 4, 5 or 6;

$Q_1$ is:
an amino acid amide of an amino acid with a carboxylic acid in the side chain, or an amino acid with an uncharged side chain, which residue forms, with its carboxylic acid group, an amide group together with the α-amino group of the N-terminal amino acid residue of the B chain of Ins or together with the ε-amino group of a Lys residue present in the A or B chain of Ins, or
a chain composed of two, three or four α-amino acid amide or amino acid residues linked together via amide bonds, which chain—via an amide bond—is linked to the α-amino group of the N-terminal amino acid residue of the B chain of Ins or to the ε-amino group of a Lys residue present in the A or B chain of Ins, or
a bond $Q_2$ is:
—$COCH(CONH_2)$—
—$COCH_2N(CH_2CONH_2)$—
—$COCH_2N(CH_2CONH_2)COCH_2N(CH_2CONH_2)$—
—$COCH_2CH_2N(CH_2CH_2CONH_2)$—
—$COCH_2CH_2N(CH_2CH_2CONH_2)$—$COCH_2CH_2N(CH_2CH_2CONH_2)$—
—$COCH_2N(CH_2CH_2CONH_2)$—
—$COCH_2CH_2N(CH_2CONH_2)$—
—$COCH_2OCH_2CONH$—
—$CO$—$((CR^5R^6)_{1-6}$—NH—CO$)_{1-4}$;
—$CO$—$((CR^5R^6)_{1-6}$—CO—NH$)_{1-4}$—, where $R^5$ independently can be H, —$CH_3$, —$(CH_2)_{1-6}CH_3$ or —$CONH_2$ and $R^6$ independently can be H, —$CH_3$, —$(CH_2)_{1-6}CH_3$; or
a bond provided that
at least one of $Q_1$ or $Q_2$ is not a bond, and
that $Q_2$ is not —CO—$(CH_2)_2$—CO—NH— when n is 0 or 1, $X_1$ is a bond and $Q_3$ is $(CH_2CH_2O)_2$—, $(CH_2CH_2O)_3$— or $(CH_2CH_2OCH_2CH_2CH_2CH_2O)$— and that if an amine in $Q_1$ or $Q_2$ forms a bond with the rest of the substituent, the amine must be bound to the rest of the substituent via a carbonyl group;

$Q_3$, $Q_4$, and $Q_5$ independently of each other can be
—$(CH_2)_m$— where m is an integer in the range of 6 to 32;
a divalent hydrocarbon chain comprising 1, 2 or 3 —CH═CH— groups and a number of —$CH_2$— groups sufficient to give a total number of carbon atoms in the chain in the range of 4 to 32;
—$CO$—$((CR^5R^6)_{1-6}$—NH—CO)—;
—$(CO$—$(CR^5R^6)_{1-6}$—CO—NH$)_{1-4}$—, where $R^5$ independently can be H, —$CH_3$, —$(CH_2)_{1-6}CH_3$ or —$CONH_2$ and $R^6$ independently can be H, —$CH_3$, —$(CH_2)_{1-6}CH_3$;
—CO—$(CH_2)_{0-3}$—Ar—$(CH_2)_{0-3}$— where Ar can be arylene or heteroarylene, which may be substituted with one or two groups selected from the group consisting of —$CH_3$, —$(CH)_{1-6}$—$CH_3$, —$CONR^1R^2$ or —$SO_2NR^1R^2$, where $R^1$ and $R^2$, independently of each other can be H, —$CH_3$ or —$(CH)_{1-6}$—$CH_3$;
$(CH_2CH_2O)_y$—; $(CH_2CH_2CH_2O)_y$—; $(CH_2CH_2CH_2CH_2O)_y$—;
$(CH_2CH_2OCH_2CH_2CH_2CH_2O)_y$— or $(CH_2CH_2CH_2OCH_2CH_2CH_2CH_2O)_y$—;
—$(CH_2OCH_2)_y$— where y is 1-20;
arylene or heteroarylene, which may be substituted with one or two groups selected from the group consisting of —$CH_3$, —$(CH)_{1-6}$—$CH_3$, —$CONR^1R^2$ or —$SO_2NR^1R^2$, where $R^1$ and $R^2$, independently of each other can be H, —$CH_3$ or —$(CH)_{1-6}$—$CH_3$;

a chain of the formula

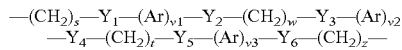

wherein Ar is defined as above, $Y_1$-$Y_6$ independently of each other can be O, S, S=O, $SO_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—$(CH_2)_1$—O— does not occur; or a bond;

with the proviso that at least one of $Q_3$-$Q_5$ is not a bond; $X_1$, $X_2$ and $X_3$ are independently of each other O;
—C=O
a bond;
$NCOR^1$, where $R^1$ can be H, —$CH_3$ or —$(CH)_{1-6}$—$CH_3$; or

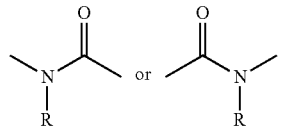

where R is hydrogen, $C_{1-3}$-alkyl, $C_{2-3}$-alkenyl or $C_{2-3}$-alkynyl;

with the proviso that $X_1$, $X_2$ and $X_3$ cannot bind to Z and when $X_1$, $X_2$ and $X_3$ are O, then $X_1$, $X_2$ and $X_3$ do not bind directly to O in $Q_3$, $Q_4$, and $Q_5$ and Z is: —COOH; —CO-Asp; —CO-Glu; —CO-Gly; —CO-Sar; —$CH(COOH)_2$; —$N(CH_2COOH)_2$; —$SO_3H$; —$OSO_3H$; —$OPO3H_2$; —$PO_3H_2$; -tetrazol-5-yl or —O—$W_1$, where $W_1$ is arylene or heteroarylene, which may be substituted with one or two groups selected from the group consisting of tetrazo-5-lyl, —COOH, —$SO_3H$, —$(CH_2)_{1-6}$—$SO_3H$, —$(CH_2)_{1-6}$—O—$PO_3H_2$, —$CONR^3R^4$ or —$SO_2NR^3R^4$, where $R^3$ and $R^4$, independently of each other can be H, —$(CH_2)_{1-6}$—$SO_3H$, or —$(CH_2)_{1-6}$—O—$PO_3H_2$; provided that when Z is —O—$W_1$ then $Q_1$ must be present and any $Zn^{2+}$ complex thereof.

\* \* \* \* \*

UNITED STATES PATENT AND TRADEMARK OFFICE
CERTIFICATE OF CORRECTION

PATENT NO. : 9,447,163 B2  
APPLICATION NO. : 13/980969  
DATED : September 20, 2016  
INVENTOR(S) : Joergen M. Mollerup et al.

Page 1 of 1

It is certified that error appears in the above-identified patent and that said Letters Patent is hereby corrected as shown below:

In the Claims:

At column 36, claim number 3, beginning at line number 10, please amend as follows:

3. The process of claim 1, wherein the divalent metal ion is zinc$^{2+}$ and the concentration of the zinc ions in the solution is in the range of 0.01-200 mM.

Signed and Sealed this  
Thirteenth Day of December, 2016

Michelle K. Lee  
*Director of the United States Patent and Trademark Office*